US00RE38330E

(19) United States
(12) Reissued Patent
Cerami et al.

(10) Patent Number: US RE38,330 E
(45) Date of Reissued Patent: Nov. 25, 2003

(54) PREVENTING AND REVERSING ADVANCED GLYCOSYLATION ENDPRODUCTS

(75) Inventors: Anthony Cerami, Shelter Island, NY (US); Peter C. Ulrich, Old Tappan, NJ (US); Dilip R. Wagle, Valley Cottage, NY (US); San-Bao Hwang, Sudbury, MA (US); Sara Vasan, Yonkers, NY (US); John J. Egan, New York City, NY (US)

(73) Assignee: Alteon Inc., Ramsey, NJ (US)

( * ) Notice: This patent is subject to a terminal disclaimer.

(21) Appl. No.: 09/373,345

(22) Filed: Aug. 12, 1999

Related U.S. Patent Documents

Reissue of:
(64) Patent No.: 5,656,261
Issued: Aug. 12, 1997
Appl. No.: 08/375,155
Filed: Jan. 18, 1995

(51) Int. Cl.[7] ..... A61K 7/20; A61K 31/425; A61K 7/22; C07D 277/28; C07D 277/62

(52) U.S. Cl. ..... 424/53; 424/51; 424/52; 424/54; 424/56; 514/365; 514/367; 548/152; 548/161; 548/164; 548/179; 548/180; 548/205; 548/190; 548/193; 548/194; 548/202; 544/140; 544/296; 546/256; 546/199; 546/211

(58) Field of Search ..... 424/53, 51, 52, 424/54, 56; 514/365, 367; 548/152, 161, 164, 179, 180, 190, 193, 194, 202, 203, 204, 205, 312.4, 302.7, 365.4, 364.7; 544/140, 296; 546/256, 199, 211

(56) References Cited

U.S. PATENT DOCUMENTS

| | | | | | |
|---|---|---|---|---|---|
| 4,609,670 | A | * | 9/1986 | Dominianni et al. | 548/399 |
| 4,683,312 | A | * | 7/1987 | Dominianni et al. | 548/341 |
| 4,758,583 | A | * | 7/1988 | Cerami et al. | 514/399 |
| 5,108,930 | A | | 4/1992 | Ulrich et al. | 436/111 |
| 5,230,998 | A | | 7/1993 | Neurath et al. | 435/7 |
| 5,262,152 | A | | 11/1993 | Ulrich et al. | 424/54 |
| 5,366,885 | A | | 11/1994 | Barranco, III | 435/6 |
| 5,853,703 | A | | 12/1998 | Cerami et al. | 424/53 |
| 6,007,865 | A | | 12/1999 | Cerami et al. | 426/656 |
| 6,121,300 | A | | 9/2000 | Wagle et al. | 514/365 |

FOREIGN PATENT DOCUMENTS

| | | |
|---|---|---|
| DE | 2323465 | 11/1973 |
| EP | 167139 | 1/1986 |
| EP | 364344 A2 | 4/1990 |
| EP | 364344 A3 | 4/1990 |
| EP | 586806 | 3/1994 |
| EP | 614886 | 9/1994 |
| JP | 60-184038 | 9/1985 |
| JP | 1143855 | 6/1989 |
| WO | WO 94/11490 A3 | 5/1994 |
| WO | WO 94/11490 A2 | 5/1994 |
| WO | WO94/20083 | 9/1994 |

OTHER PUBLICATIONS

Makita, et al., J. Biol. Chem., vol. 267, pp. 5133–5138; 1992.
Chang, et al., J. Biol. Chem., vol. 260, pp. 7970–7974; 1985.
Ulrich, et al., Modern Aging Res., vol. 7, pp. 83–92; 1985.
Ponger, et al., Proc. Natl. Acad. Sci USA, vol. 81, pp. 2684–2688; 1984.
Kawakishi, et al., Maillard React. Chem. Food Health, vol. 151, pp. 281–285; 1994.
Tsuge, et al., Chem. Lett., vol. 5, pp. 711–714; 1982.
Archer, et al., J. Med. Chem., vol. 22, pp. 306–309; 1979.
Singh, et al., Tetrahedron, vol. 48, pp. 4545–4550; 1992.
Gandaseugi, et al., Heterocycles, vol. 31, pp. 1801–1809; 1990.
"Heterocyclic Analogs of Azulene" Ukr. Khim. Zh. 30(6), 488–495, 1964 (CA Abstract Provided).
"Mechanism of cleavage of acetylbenzoyl in method catalyzed by thiazolium salts" Ukr. Khim. Zh. 51:521–525, 1985 (translation provided).
Galera et al., J. Heterocyclic Chem., 23, 1889–1892 (1986).
CA 113: 132169y Preparation . . . Inhibitors, Sohda et al., p. 652, 1990.*
CA 113: 191334w Preparation . . . Agents. Sohda et al., p. 723, 1990.*
CA 118:15815y Species . . . 4–Hydroxbiphenyl. Yoshimura et al., p. 12, 1993.*
CA 120: 173495q Use . . . Glycosylation. Schoenafinger et al., p. 682, 1994.*
Dominianni et al. (1989) J. Med. Chem. 32:2301–6.*
Brownlee et al., "Aminoguanidine prevents diabetes–induced arterial wall protein cross–linking", Science 232;1629–1632 (1986).*
Brownlee et al., "Inhibition of glucose–derived protein crosslinking and prevention of early diabetic changes in glomelular basement membrane by aminoguanidine", Diabetes 35 (Suppl. 1):42A (1986) (abstract #166).*

(List continued on next page.)

*Primary Examiner*—Joseph K. McKane
*Assistant Examiner*—Ebenezer Sackey
(74) *Attorney, Agent, or Firm*—Ivor R. Elrifi, Ph.D.; Matthew J. Golden; Mintz, Levin, Cohn, Ferris, Glovsky & Popeo, P.C.

(57) ABSTRACT

The present invention relates to compositions and methods for inhibiting and reversing nonenzymatic cross-linking (protein aging). Accordingly, a composition is disclosed which comprises a thiazolium compound capable of inhibiting, and to some extent reversing, the formation of advanced glycosylation endproducts of target proteins by reacting with the carbonyl moiety of the early glycosylation product of such target proteins formed by their initial glycosylation. The method comprises contacting the target protein with the composition. Both industrial and therapeutic applications for the invention are envisioned, as food spoilage and animal protein aging can be treated. A novel immunoassay for detection of the reversal of the nonenzymatic crosslinking is also disclosed.

234 Claims, No Drawings

OTHER PUBLICATIONS

Bucala et al., "Advanced Glycosylation: Chemistry, Biology, and Implications for Diabetes and Aging" in Advances in Pharmacology, vol. 23, pp. 1–34, Academic Press (1992).*

Eble et al., "Nonenzymatic glucosylation and glucose–dependent cross–linking of protein", J. Biol. Chem. 258:9406–9412 (1983).*

Hayase et al, "Aging of proteins: Immunological detection of a glucose–derived pyrrole formed during Maillard reaction in vivo", J. Biol. Chem. 263: 3758–3764 (1989).*

Nicholls et al., "Advanced glycosylaton end–products in experimental murine diabetic nephropathy: Effect of islet isografting and of aminoguanidine", Lab. Invest. 60:486–91(1989).*

Nordbo, "Ability of chlorhexidine an benzalkonium chloride to catalyze browning reactions in vivo", J. Dent. Res. 58:1429 (1979).*

Oimomi et al, "The effects of aminoguanidine on 3–deoxyglucosone in the Maillard reaction", Agric. Biol. Chem. 53:1727–1728 (1989).*

Oimomi et al., "Aminoguanidine inhibits 3–deoxyglucosone during the advanced Maillard reaction", Diabetes Res. Clin. Practice 6:311–313 (1989).*

Potts et al., "Bridgehead nitrogen systems. X. Cycloadditions eith thiazolium N–ylides", J. Org. Chem. 41:187–191 (1976).*

Potts et al., "Cycloaddition of N–iminothiazolium ylides with acetylenic dipolarophiles. Formation of pyrazoles", J. Org. Chem. 42:1648–9 (1977).*

Sell and Monnier, "Structure elucidation of a senescence cross–link from human extracellular matrix", J. Biol. Chem. 264:21597–21602 (1989).*

Tamura et al., "O–Mesitylenseulfonylhydroxylamine and related compounds–powerful aminating reagents", Synthesis 1:1–17 (1977).*

* cited by examiner

PREVENTING AND REVERSING ADVANCED GLYCOSYLATION ENDPRODUCTS

Matter enclosed in heavy brackets [ ] appears in the original patent but forms no part of this reissue specification; matter printed in italics indicates the additions made by reissue.

BACKGROUND OF THE INVENTION

The present invention relates generally to the aging of proteins resulting from their reaction with glucose and other reducing sugars and more particularly to the inhibition of the reaction of nonenzymatically glycosylated proteins and the reversal of the often resultant formation of advanced glycosylation (glycation) endproducts and cross-links.

The reaction between glucose and proteins has been known for some time. Its earlier manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin Alc. The reaction has also been found to occur with a variety of other body proteins, such as lens crystallins, collagen and nerve proteins. See Bucala et al., "Advanced Glycosylation; Chemistry, Biology, and Implications for Diabetes and Aging" in Advances in Pharmacology, Vol. 23. pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In U.S. Pat No. 4,758,583, a method and associated agents were disclosed that served to inhibit the formation of advanced glycosylation endproducts by reacting with an early glycosylation product that results from the original reaction between the target protein and glucose. Accordingly, inhibition was postulated to take place as the reaction between the inhibitor and the early glycosylation product appeared to interrupt the subsequent reaction of the glycosylated protein with additional protein material to form the cross-linked late-stage product. One of the agents identified as an inhibitor was aminoguanidine, and the results of further testing have borne out its efficacy in this regard.

While the success that has been achieved with aminoguanidine and similar compounds is promising, a need continues to exist to identify and develop additional inhibitors that broaden the availability and perhaps the scope of this potential activity and its diagnostic and therapeutic utility. A further need exists to find agents which not only inhibit this reaction and its consequences, but agents capable of reversing the already formed advanced glycosylation endproducts, thereby reversing the resultant effects thereof.

SUMMARY OF THE INVENTION

In accordance with the present invention, a method and compositions are disclosed for the inhibition and reversal of the advanced glycosylation of proteins (protein aging). In particular, the compositions comprise agents for inhibiting the formation of and reversing the pre-formed advanced glycosylation (glycation) endproducts and cross-linking. The agents are members of the class of compounds known as thiazoliums. Advanced glycation endproducts and cross-linking caused by other reactive sugars present in vivo or in foodstuffs, including ribose, galactose and fructose would also be prevented and reversed by the methods and compositions of the present invention.

The agents comprise thiazolium compounds having the following structural formula:

(I)

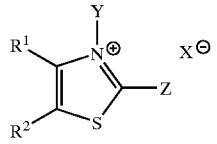

wherein $R^1$ and $R^2$ are independently selected from the group consisting of hydrogen, hydroxy(lower) alkyl, lower alkyl, or $R^1$ and $R^2$ together with their ring carbons may be an aromatic fused, ring;

Z is hydrogen or an amino group;

Y is amino, a group of the formula

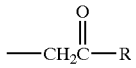

wherein R is a lower alkyl, alkoxy, hydroxy, amino or aryl group;

or a group of the formula $—CH_2R'$ wherein R' is hydrogen, or a lower alkyl, lower alkynyl, or aryl group;

X is a halide, tosylate, methanesulfonate or mesitylenesulfonate ion;

and mixtures thereof, and a carrier therefor.

The compounds, and their compositions, utilized in this invention appear to react with an early glycosylation product thereby preventing the same from later forming the advanced glycosylation end products which lead to protein cross-links, and thereby, to protein aging, and further, react with already formed advanced glycosylation end products to reduce the amount of such products.

The present invention also relates to a method for inhibiting protein aging by contacting the initially glycosylated protein at the stage of the early glycosylation product with a quantity of one or more of the agents of the present invention, or a composition containing the same, and to a method for breaking the already formed advanced glycosylation end products to reduce the amount of such products. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs, and to reverse the effects of already formed advanced glycosylation end products.

The ability to inhibit the formation of advanced glycosylation endproducts, and to reverse the already formed advanced glycosylation products in the body carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts, and to reduce the amount of already formed advanced glycosylation endproducts in the body carries the promise of treatment for diabetes and, of course, improving the quality and, perhaps, duration of animal and human life.

The present agents are also useful in the area of personal appearance and hygiene, as they prevent, and reverse, the staining of teeth by cationic anti-microbial agents with anti-plaque properties, such as chlorhexidine.

The invention additionally comprises a novel analytic method for the determination of the "breaking" or reversal of the formation of non-enzymatic endproducts.

Accordingly, it is a principal object of the present invention to provide a method for inhibiting the formation of advanced glycosylation endproducts and extensive cross-linking of proteins, and a method of reversing the already formed advanced glycosylation endproducts and cross-links, that occur as an ultimate consequence of the reaction of the proteins with glucose and other reactive sugars, by correspondingly inhibiting the formation of advanced glycosylation endproducts, and reversing the advanced glycosylation that has previously occurred.

It is a further object of the present invention to provide a method as aforesaid which is characterized by a reaction with an initially glycosylated protein identified as an early glycosylation product.

It is a further object of the present invention to provide a method as aforesaid which prevents the rearrangement and cross-linking of the said early glycosylation products to form the said advanced glycosylation endproducts.

It is a yet further object of the present invention to provide agents capable of participating in the reaction with the said early glycosylation products in the method as aforesaid.

It is a yet further object of the present invention to provide agents which break or reverse the advanced glycosylation endproducts formed as a consequence of the aforesaid advanced glycosylation reaction sequence.

It is a still further object of the present invention to provide therapeutic methods of treating the adverse consequences of protein aging by resort to the aforesaid method and agent.

It is a still further object of the present invention to provide a method of inhibiting, and reversing, the discoloration of teeth by resort to the aforesaid method and agents.

It is a still further object of the present invention to provide compositions, including pharmaceutical compositions, all incorporating the agents of the present invention.

It is still further object of the present invention to provide novel compounds, as well as processes for their preparation, for use in the methods and compositions of the present invention.

It is a still further object of the present invention to provide a novel immunoassay which can be utilized to detect compounds having the ability to "break" or reverse the formation of non-enzymatic glycosylation endproducts.

Other objects and advantages will become apparent to those skilled in the art from a consideration of the ensuring description.

DETAILED DESCRIPTION OF THE PREFERRED EMBODIMENTS

In accordance with the present invention, agents, compositions including pharmaceutical compositions containing said agents and associated methods have been developed which are believed to inhibit the formation of advanced glycosylation endproducts in a number of target proteins existing in both animals and plant material, and to reverse the already formed advanced glycosylation endproducts. In particular, the invention relates to a composition which may contain one or more agents comprising thiamine compounds having the structural formula (I)

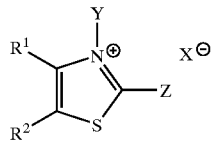

wherein $R^1$ and $R^2$ are independently selected from the group consisting of hydrogen, hydroxy(lower) alkyl, lower acyloxy(lower)alkyl, lower alkyl, or $R^1$ and $R^2$ together with their ring carbons may be an aromatic fused ring;

Z is hydrogen or an amino group;

Y is hydrogen, or a group of the formula

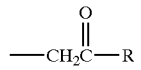

wherein R is a lower alkyl, alkoxy, hydroxy, amino or aryl group;

or a group of the formula $—CH_2R'$ wherein R' is hydrogen, or a lower alkyl, lower alkynyl, or aryl group;

X is a halide, tosylate, methanesulfonate or mesitylenesulfonate ion;

and mixtures thereof, and a carrier therefor.

The lower alkyl groups referred to above contain 1–6 carbon atoms and include methyl, ethyl, propyl, butyl, pentyl, hexyl, and the corresponding branched-chain isomers thereof. The lower alkynyl groups contain from 2 to 6 carbon atoms. Similarly, the lower alkoxy groups contain from 1 to 6 carbon atoms, and include methoxy, ethoxy, propoxy, butoxy, pentoxy, and hexoxy, and the corresponding branched-chain isomers thereof. These groups are optionally substituted by one or more halo, hydroxy, amino or lower alkylamino groups.

The lower acyloxy(lower)alkyl groups encompassed by the above formula include those wherein the acyloxy portion contain from 2 to 6 carbon atoms and the lower alkyl portion contains from 1 to 6 carbon atoms. Typical acyloxy portions are those such as acetoxy or ethanoyloxy, propanoyloxy, butanoyloxy, pentanoyloxy, hexanoyloxy, and the corresponding branched chain isomers thereof. Typical lower alkyl portions are as described hereinabove. The aryl groups encompassed by the above formula are those containing 6–10 carbon atoms, such as phenyl and lower alkyl substituted-phenyl e.g., tolyl and xylyl, and are optionally substituted by 1–2 halo, hydroxy, lower alkoxy or di(lower) alkylamino groups. Preferred aryl groups are phenyl, methoxyphenyt and 4-bromophenyl groups.

The halo atoms in the above formula may be fluoro, chloro, bromo or iodo.

For the purposes of this invention, the compounds of formula (I) are formed as biologically and pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions.

Of the compounds encompassed by Formula I, certain substituents are preferred. For instance, the compounds wherein $R_1$ or $R_2$ are lower alkyl groups are preferred. Also highly preferred are the compounds wherein Y is a 2-phenyl-2-oxoethyl or a 2-[4'-bromophenyl]-2-oxoethyl group.

Representative compounds of the present invention are:

3-aminothiazolium mesitylenesulfonate;

3-amino-4,5-dimethylaminothiazolium mesitylenesulfonate;

2,3-diaminothiazolinium mesitylenesulfonate;

3-(2-methoxy-2-oxoethyl)-thiazolium bromide;

3-(2-methoxy-2-oxoethyl)-4,5-dimethylthiazolium bromide;

3-(2-methoxy-2-oxoethyl)-4-methylthiazolium bromide:

3-(2-phenyl-2-oxoethyl)-4-methylthizolium bromide;

3-(2-phenyl-2-oxoethyl)-4,5-dimethylthiazolium bromide;

3-amino-4-methylthiazolium mesitylenesulfonate;

3-(2-methoxy-2-oxoethyl)-5-methylthiazolium bromide;

3-(3-(2-phenyl-2-oxoethyl)-5-methylthiazolium bromide;

3-[2-(4'-bromophenyl)-2-oxoethyl]thiazolium bromide;

3-[2-(4'-bromophenyl)-2-oxoethyl]-4-methylthiazolium bromide;

3-[2-(4'-bromophenyl)-2-oxoethyl]-5-methylthiazolium bromide;

3-[2-(4'bromophenyl)-2-oxoethyl]-4,5-dimethylthiazolium bromide;

3-(2-methoxy-2-oxoethyl)-4-methyl-5-(2-hydroxyethyl) thiazolium bromide;

3-(2-phenyl-2-oxoethyl)-4-methyl-5-(2-hydroxyethyl) thiazolium bromide;

3-[2-(4'-bromophenyl)-2-oxoethyl]-4-methyl-5-(2-hydroxyethyl)thiazolium bromide;

3,4-dimethyl-5-(2-hydroxyethyl)thiazolium iodide;

3-ethyl-5-(2-hydroxyethyl)-4-methylthiazolium bromide;

3-benzyl-5-(2-hydroxyethyl)-4-methylthiazolium chloride;

3-(2-methoxy-2-oxoethyl)benzothiazolium bromide;

3-(2-phenyl-2-oxoethyl)benzothiazolium bromide;

3-[2-(4'bromophenyl)-2-oxoethyl]benzothiazolium bromide;

3-(carboxymethyl)benzothiazolium bromide;

2,3-(diamino)benzothiazolium mesitylenesulfonate;

3-(2-amino-2-oxoethyl)thiazolium bromide;

3-(2-amino-2-oxoethyl)-4-methylthiazolium bromide;

3-(2-amino-2-oxoethyl)-5-methylthiazolium bromide;

3-(2-amino-2-oxoethyl)4,5-dimethylthiazolium bromide;

3-(2-amino-2- oxoethyl) benzothiazolium bromide;

3-(2-amino-2- oxoethyl) 4-methyl-5-(2-hydroxyethyl) thiazolium bromide;

3-amino-5-(2-hydroxyethyl)-4-methylthiazolium mesitylenesulfonate;

3-(2-methyl-2-oxoethyl)thiazolium chloride;

3-amino-4-methyl-5-(2-acetoxyethyl)thiazolium mesitylenesulfonate;

3-(2-phenyl-2-oxoethyl)thiazolium bromide;

3-(2-methoxy-2-oxoethyl)-4-methyl-5-(2-acetoxyethyl) thiazolium bromide;

3-(2-amino-2-oxoethyl)-4-methyl-5-(2-acetoxyethyl) thiazolium bromide;

2-amino-3-(2-methoxy-2-oxoethyl)thiazolium bromide;

2-amino-3-(2-methoxy-2-oxoethyl)benzothiazolium bromide;

2-amino-3-(2-amino-2-oxoethyl)thiazolium bromide;

2-amino-3-(2-amino-2-oxoethyl)benzothiazolium bromide;

3-[2-(4'-methoxyphenyl)-2-oxoethyl]-thiazolinium bromide;

3-[2-(2',4'-dimethoxyphenyl)-2-oxoethyl]-thiazolinium bromide;

3-[2-(4'-fluorophenyl)-2-oxoethyl]-thiazolinium bromide;

3-[2-(2',4'-difluorophenyl)-2-oxoethyl]-thiazolinium bromide;

3-[2-(4'-diethylaminophenyl)-2-oxoethyl]-thiazolinium bromide;

3-propargyl-thiazolinium bromide;

3-propargyl-4-methylthiazolinium bromide;

3-propargyl-5-methylthiazolinium bromide;

3-propargyl-4,5-dimethylthiazolinium bromide; and 3-propargyl-4-methyl-5-(2-hydroxyethyl)-thiazolinium bromide.

Certain of the compounds represented by Formula I are novel compounds which represent a further embodiment of the present invention. These compounds are represented by the formula (Ia)

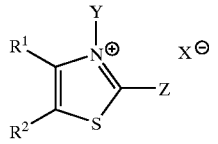

wherein Y and Z are both amino groups and $R^1$ and $R^2$ are as hereinbefore defined; and X is a halide, tosylate, methanesulfonate or mesitylenesulfonate ion.

The above compounds are capable of inhibiting the formation of advanced glycosylation endproducts on target proteins, as well as being capable of breaking or reversing already formed advanced glycosylation endproducts on such proteins. The cross-linking of the protein to form the advanced glycosylation endproduct contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible. Thus, the compounds employed in accordance with this invention inhibit this late-stage Maillard effect and intervene in the deleterious changes described above, and reverse the level of the advanced glycosylation endproducts already present in the protein material.

The rationale of the present invention is to use agents which block, as well as reverse, the post-glycosylation step, i.e., the formation of fluorescent chromophores, the presence of which chromophores is associated with, and leads to adverse sequelae of diabetic complications and aging. An ideal agent would prevent the formation of the chromophore and its associated cross-links of proteins to proteins and trapping of proteins on the other proteins, such as occurs in arteries and in the kidney, and reverse the level of such cross-link formation already present.

The chemical nature of the early glycosylation products with which the compounds of the present invention are believed to react may vary, and accordingly the term "early glycosylation product(s)" as used herein is intended to include any and all such variations within its scope. For example, early glycosylation products with carbonyl moieties that are involved in the formation of advanced glycosylation endproducts, and that may be blocked by reaction with the compounds of the present invention, have been postulated. In one embodiment, it is envisioned that the early glycosylation product may comprise the reactive carbonyl moieties of Amadori products or their further condensation, dehydration and/or rearrangement products, which may condense to form advanced glycosylation endproducts. In another scenario, reactive carbonyl compounds, containing one or more carbonyl moieties (such as glycolaldehyde, glyceraldehyde or 3-deoxyglucosone) may form from the cleavage of Amadori or other early glycosylation endproducts, and by subsequent reactions with an amine or Amadori product, may form carbonyl containing advanced glycosylation products such as alkylformylglycosylpyrroles.

Several investigators have studied the mechanism of advanced glycosylation product formation. In vitro studies by Eble et al., (1983), "Nonenzymatic Glucosylaton and Glucose-dependent Cross-linking of Protein", J. Biol. Chem., 258: 9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNAase as a model system, which was then examined under varying conditions. In one aspect, the glycosylated protein material was isolated and placed in a glucose-free environment and thereby observed to determine the extent of cross-linking.

Eble et al. thereby observed that cross-linking continued to occur not only with the glycosylated protein but with non-glycosylated proteins as well. One of the observations noted by Eble et al. was that the reaction between glycosylated protein and the protein material appeared to occur at the location on the amino acid side-chain of the protein. Confirmatory experimentation conducted by Eble et al. in this connection demonstrated that free lysine would compete with the lysine on RNAase for the binding of glycosylated protein. Thus, it might be inferred from these data that lysine may serve as an inhibitor of advanced glycosylation; however, this conclusion and the underlying observations leading to it should be taken in the relatively limited context of the model system prepared and examined by Eble et al. Clearly, Eble et al. does not appreciate, nor is there a suggestion therein, of the discoveries that underlie the present invention, with respect to the inhibition of advanced glycosylation of proteins both in vitro and in vivo.

The experiments of Eble et al. do not suggest the reactive cleavage product mechanism or any other mechanism in the in vivo formation of advanced glycosylation endproducts in which glucose is always present. In fact, other investigators support this mechanism to explain the formation of advanced glycosylated endproducts in vivo (see for example Hayase et al, J. Biol. Chem., 263, pp. 3758–3764 (1989); Sell and Monnier, J. Biol. Chem. 264, pp. 21597–21602 (1989); Oimomi et al., Agric. Biol. Chem., .53(6): 1727–1728 (1989); and Diabetes Research and Clinical Practice, 6: 311–313 (1989). Accordingly, the use of lysine as an inhibitor in the Eble et al. model system has no bearing upon the utility of the compounds of the present invention in the inhibition of advanced glycosylated endproducts formation in the presence of glucose in vivo, and the amelioration of complications of diabetes and aging.

The present invention likewise relates to methods for inhibiting the formation of advanced glycosylation endproducts, and reversing the level of already formed advanced glycosylation endproducts, which comprise contacting the target proteins with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

As is apparent from a discussion of the environment of the present invention, the present methods and compositions hold the promise for arresting, and to some extent reversing, the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers.

Replacement of currently-used preservatives, such as sulfur dioxide known to cause allergies and asthma in humans, with non-toxic, biocompatible compounds is a further advantage of the present invention.

The therapeutic implications of the present invention relate to the arrest, and to some extent, the reversal of the aging process which has, as indicated earlier, been identified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this may result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of glucose-derived cross-links. Such diabetic microvascular changes and microvascular occlusion can be effectively prevented and reversed by chemical inhibition and reversal of the advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., Lab. Invest., 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., Science, 232, pp. 1629–1632 (1986) to this additional target organ of complication of diabetes. Also, an additional study showed the reduction of immunoglobulin trapping in the kidney by aminoguanidine (Brownlee et al., Diabetes, 35 Suppl. 1, p. 42A (1986)).

Further evidence in the streptozotocin-diabetic rat model that aminoguanidine administration intervenes in the development of diabetic nephropathy was presented by Brownlee et al., 1988, supra, with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition and reversal of the formation of advanced glycosylation endproducts (AGEs), by the teaching of the present invention, may prevent, as well as to some extent reverse late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of Formula I may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 30 mg/kg.

As noted earlier, the invention also extends to a method of inhibiting and reversing the discoloration of teeth resulting from nonenzymatic browning in the oral cavity which comprises administration to a subject in need of such therapy an amount effective to inhibit and reverse the formation of advanced glycosylation endproducts of a composition comprising an agent of structural Formula I.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, J. Dent. Res., 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of Formula I are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent of Formula I is formulated in compositions in an amount effective to inhibit and reverse the formation of advanced glycosylation endproducts. This amount will, of course, vary with the particular agent being utilized and the particular dosage form, but typically is in the range of 0.01% to 1.0%, by weight, of the particular formulation.

The compounds encompassed by Formula I are conveniently prepared by chemical syntheses well-known in the art. Certain of the compounds encompassed by Formula I are well-known compounds readily available from chemical supply houses and/or are preparable by synthetic methods specifically published therefor. For instance, 3,4-dimethyl-5-(2-hydroxyethyl)thiazolium iodide; 3-ethyl-5-(2-hydroxyethyl)-4-methylthiazolium bromide; 3-benzyl-5-(2-hydroxyethyl)-4-methylthiazolium chloride; and 3-(carboxymethyl)benzothiazolium bromide are obtainable from Aldrich Chem. Co.

Compounds described in the chemical and patent literature or directly preparable by methods described therein and encompassed by Formula I are those such as 3-(2-phenyl-2-oxoethyl)-4-methylthiazolium bromide and 3-(2-phenyl-2-oxoethyl)-4-methylthiazolium bromide [Potts et al. J. Org. Chem, 41, pp. 187–191 (1976)].

Certain of the compounds of formula (I) are novel compounds, not heretofore known in the art. These compounds are those represented by the formula Ia (Ia)

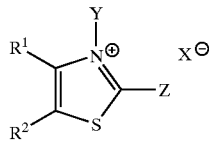

wherein Y and Z are both amino groups and $R^1$ and $R^2$ are independently selected from the group consisting of hydrogen, hydroxy(lower)alkyl, lower alkyl, or $R^1$ and $R^2$ together with their ring carbons may be an aromatic fused ring; and X is a halide, tosylate, methanesulfonate or mesitylenesulfonate ion. Other novel compounds are those of formula I wherein Y is a lower alkynylmethyl group or a 2-amino-2-oxoethyl group.

The compounds of formula I wherein Y is a group of the formula (I)

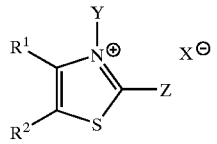

wherein R is a lower alkyl, alkoxy, hydroxy, amino or aryl group;

or a group of the formula —$CH_2R'$ wherein R' is hydrogen, or a lower alkyl, lower alkynyl or aryl group;

X is a halide, tosylate, methanesulfonate or mesitylenesulfonate ion;

can be prepared according to the methods described in Potts et al., J. Org. Chem., 41, 187 (1976); and Potts et al., J. Org. Chem., 42, 1648 (1977), or as shown in Scheme I below.

Scheme I.

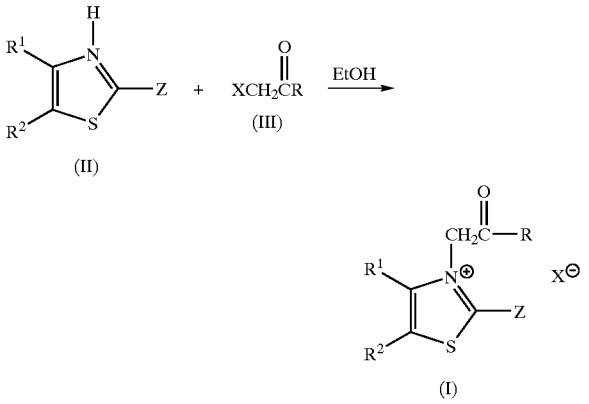

wherein $R^1$, $R^2$, Z, and R are as hereinabove defined, and X is a halogen atom.

In reaction Scheme I, the appropriate substituted thiazole compound of formula II wherein $R^1$, $R^2$ and Z are as hereinbefore defined, is reacted with the appropriate halo compound of formula III wherein R and X are as hereinbefore defined, to afford the desired compound of formula I wherein $R^1$, $R^2$, Z, R and X are as hereinbefore defined.

Typically, this reaction is conducted at reflux temperatures for times of about 1–3 hours. Typically, a polar solvent such as ethanol is utilized for the conduct of the reaction.

The compounds of formula I wherein Y is an amino group can be prepared according to the methods described in Tamura et al., Synthesis, 1 (1977), or as shown below in Scheme II.

SCHEME II

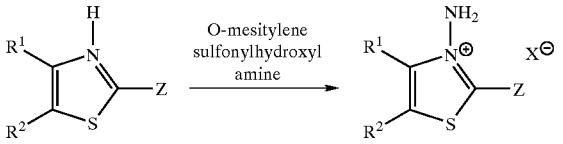

wherein $R^1$, $R^2$ and Z are as defined hereinabove.

In the reaction shown in Scheme II, typically conducted in an anhydrous polar solvent at room temperatures, typical reaction temperatures range from room temperature to reflux, and typical times vary from 1 to about 4 hours. This reaction affords the mesitylene sulfonate, which can then be optionally converted to other thiazolium salts by typical exchange reactions.

The present invention also involves a novel sandwich enzyme immunoassay used to ascertain the ability of test compounds to "break" or reverse already formed advanced glycosylation endproducts by detecting the breaking of AGE (Advanced glycosylation endproduct) moieties from AGE-crosslinked protein. This assay comprises:

a) incubation of AGE-modified bovine serum albumin (AGE-BSA) on collagen-coated wells of microtiter plates for a period of 2–6 hours at a temperature of 37° C.;

b) washing of the wells with PBS-Tween;

c) application of the test compounds to the washed wells of step b;

d) incubation of the test compounds applied to the washed wells for an additional 12–24 hours at a temperature of about 37° C.; and e) detection of the AGE-breaking using an antibody raised against AGE-ribonuclease or cross-link breaking with an antibody against BSA.

The following examples are illustrative of the invention.

EXAMPLE 1

3-(2-Methoxy-2-oxoethyl)thiazolium bromide

Thiazole, (850 mg, 10 mmol), methyl bromoacetate (1.52, 10 mmol) and absolute ethanol (50 ml) were refluxed for 2 hours. On cooling, the salt separated and was recrystallized from absolute ethanol to give the title compound (1.59 g), m.p. 189°–190° C. (dec).

EXAMPLE 2

3-Amino-4,5-dimethylthiazolium mesitylenesulfonate

An ice cold solution of the 4,5-dimethyl thiazole (2.26 g, 20 mmol) in dry dichloromethane (15 ml) was treated dropwise with a solution of o-mesitylenesulfonylhydroxyamine (4.3 g, 20 mmol) in dry dichloromethane (15 ml). After stirring for 2 hours at room temperature, anhydrous ether (10 ml) was added. On cooling, colorless needles of the title product, 3-amino-4,5-dimethyl-thiazolium mesitylenesulfonate, separated (3.48 g), m.p. 165°–168° C.

EXAMPLE 3

Using the procedures described above in Examples 1 and 2, the following compounds are prepared.

(1) 3-amino-thiazolium mesitylenesulfonate, m.p. 102°–104° C.

(2) 2,3 -diamino-thiazolium mesitylenesulfonate, m.p. 173°–175° C. (dec).

(3) 3-(2-methoxy-2-oxoethyl)-4,5-dimethylthiazolium bromide. m.p. 184°–185°–200° C. (dec).

(4) 3-(2-methoxy-2-oxoethyl)-4-methylthiazolium bromide, m.p. 149°–151° C. (dec).

(5) 3-(2-phenyl-2-oxoethyl)-4-methylthiazolium bromide, m.p. 218°–220° C. (dec).

(6) 3-(2-phenyl-2-oxoethyl)-4,5-dimethylthiazolium bromide, m.p. 212°–213° C. (dec).

(7) 3-amino-4-methyl-thiazolium mesitylene sulfonate, m.p. 143°–144° C.

(8) 3-(2-methoxy-2-oxoethyl)-5-methyl-thiazolium bromide, m.p. 193°–194° C. (dec).

(9) 3-(2-phenyl-2-oxoethyl)-5-methyl-thiazolium bromide, m.p. 193°–194° C.

(10) 3-(2-[$4^1$-bromophenyl]-2-oxoethyl)-thiazolium bromide, m.p. 269°–270° C. (dec).

(11) 3-(2-[$4^1$-bromophenyl]-2-oxoethyl)-4-methyl-thiazolium bromide, m.p. 248°–249° C. (dec).

(12) 3-(2-[$4^1$-bromophenyl]-2-oxoethyl)-5-methyl-thiazolium bromide, m.p. 216°–217° C.

(13) 3-(2-[$4^1$-bromophenyl]-2-oxoethyl)-4,5-dimethylthiazolium bromide, m.p. 223°–224° C. (dec).

(14) 3-(2-methoxy-2-oxoethyl)-4-methyl-5-(2-hydroxyethyl)-thiazolium bromide, m.p. 137°–138° C.

(15) 3-(2-phenyl-2-oxoethyl)-4-methyl-5-(2-hydroxyethyl)-thiazolium bromide, m.p. 180°–181° C.

(16) 3-(2-[$4^1$-bromophenyl]-2-oxoethyl)-4-methyl-5-(2-hydroxyethyl)thiazolium bromide, m.p. 251°–252° C. (dec).

(17) 3,4-dimethyl-5-(2-hydroxyethyl)-thiazolium iodide, m.p. 85°–87° C.

(18) 3-ethyl-5-(2-hydroxyethyl)-4-methyl thiazolium bromide, m.p. 84°–85° C.

(19) 3-benzyl-5-(2-hydroxyethyl)-4-methyl thiazolium chloride, m.p. 144°–146° C.

(20) 3-(2-methoxy-2-oxoethyl)-benzothiazolium bromide, m.p. 144°–145° C. (dec).

(21) 3-(2-phenyl-2-oxoethyl)-benzothiazolium bromide, m.p. 240°–241° C. (dec).

(22) 3-(2-[$4^1$-bromophenyl)-2-oxoethyl)-benzothiazolium bromide, m.p. 261°–262° C. (dec).

(23) 3-(carboxymethyl)-benzothiazolium bromide m.p. 250° C. (dec).

(24) 2,3-diamino-benzothiazolium mesitylenesulfonate, m.p. 212°–214° C. (dec).

(25) 3-(2-amino-2-oxoethyl)-thiazolium bromide, m.p. 205°–206° C.

(26) 3-(2-amino-2-oxoethyl)-4-methyl-thiazolium bromide, m.p. 220°–222° C.

(27) 3-(2-amino-2-oxoethyl)-5-methyl-thiazolium bromide, m.p. 179°–180° C.

(28) 3-(2-amino-2-oxoethyl)-4,5-dimethyl-thiazolium bromide, m.p. 147°–148° C.

(29) 3-(2-amino-2-oxoethyl)-benzothiazolium bromide, m.p. 222°–223° C.

(30) 3-(2-amino-2-oxoethyl)-4-methyl-5-(2-hydroxyethyl)thiazolium bromide, m.p. 182°–183° C.

(31) 3-amino-5-(2-hydroxyethyl)-4-methyl-thiazolium mesitylenesulfonate, m.p. 94°–95° C. (dec).

(32) 3-(2-methyl-2-oxoethyl)thiazolium chloride, m.p. 178°–179° C.

(33) 3-amino-4-methyl-5-(2-acetoxyethyl)thiazolium mesitylenesulfonate, m.p. 118°–120° C.

(34) 3-(2-phenyl-2-oxoethyl)thiazolium bromide, m.p. 217°–218° C.

(35) 3-(2-methoxy-2-oxoethyl)-4-methyl-5-(2-acetoxyethyl)thiazolium bromide, m.p. 217°–218° C.

(36) 3-(2-amino-2-oxoethyl)-4-methyl-5-(2-acetoxyethyl)thiazolium bromide, m.p. 233°–234° C.

(37) 2-amino-3-(2-methoxy-2-oxoethyl)thiazolium bromide, m.p. 191°–192° C.

(38) 2-amino-3-(2-methoxy-2-oxoethyl)benzothiazolium bromide, m.p. 236°–237° C.

(39) 2-amino-3-(2-amino-2-oxoethyl)thiazolium bromide, m.p. 209°–210° C.

(40) 2-amino-3-(2-amino-2-oxoethyl)benzothiazolium bromide, m.p. 234°–235° C.

EXAMPLE 4

The following method was used to evaluate the ability of the compounds of the present invention to inhibit the cross-linking of glycated bovine serum albumin (AGE-BSA) to the rat tail tendon collagen coated 96-well plate.

The AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PBS) for 48 hours with additional 5 times buffer exchanges. The rat tail tendon collagen coated plate was blocked first with 300 μl of superbloc blocking buffer (Pierce #37515X) for one hour. The blocking solution was removed from the wells by washing the plate twice with PBS-Tween 20 solution (0.05% Tween 20) using a NUNC-multiprobe or Dynatec ELISA-plate washer. Cross-linking of AGE-BSA (1 to 10 μg per well depending on the batch of AGE-BSA) to rat tail tendon collagen coated plate was performed with and without the testing compound dissolved in PBS buffer at pH 7.4 at the desired concentrations by the addition of 50 μl each of the AGE-BSA diluted in PBS or in the testing compound at 37° C. for 4 hours. The unbrowned BSA in PBS buffer with or without testing compound were added to the separate wells as the blanks. The un-cross-linked AGE-BSA was then removed by washing the wells three times with PBS-Tween buffer. The cross-linked AGE-BSA to the tail tendon coated plate was then quantitated by the polyclonal antibody raised against AGE-RNase. After a one-hour incubation period, AGE antibody was removed by washing 4 times with PBS-Tween.

The bound AGE antibody was then detected with the addition of horseradish peroxidase-conjugated secondary antibody—goat anti-rabbit immunoglobulin and incubation for 30 minutes. The substrate of 2,2-azino-di(3-ethylbenzthiazoline sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows.

% inhibition={[Optical density (without compound)–optical density (with compound)]/optical density (without compound)]}×100%

The $IC_{50}$ values or the inhibition at various concentrations by test compounds is as follows:

| Test Compound | $IC_{50}$ (mM) | Relative Inhibition (at 10 mM) |
|---|---|---|
| 3-amino-4,5-dimethylaminothiazolium mesitylenesulfonate | | 69% |
| 2,3-diaminothiazolinium mesitylenesulfonate | | 27% |
| 3-(2-methoxy-2-oxoethyl)-thiazolium bromide | 0.138 | |
| 3-(2-methoxy-2-oxoethyl)-4,5-dimethylthiazolium bromide | 0.138 | |
| 3-(2-methoxy-2-oxoethyl)-4-methylthiazolium bromide | | 58% |
| 3-(2-phenyl-2-oxoethyl)-4-methylthizolium bromide | 10.3 | |
| 3-(2-phenyl-2-oxoethyl)-4,5-dimethylthiazolium bromide | 48.5 | |
| 3-amino-4-methylthiazolium mesitylenesulfonate | | 46% |
| 3-(2-methoxy-2-oxoethyl)-5-methylthiazolium bromide | 0.073 | |
| 3-(3-(2-phenyl-2-oxoethyl)-5-methylthiazolium bromide | 13.89 | |
| 3-[2-(4'-bromophenyl)-2-oxoethyl]-4-methylthiazolium bromide | | 37% |
| 3-[2-(4'bromophenyl)-2-oxoethyl]-4,5-dimethylthiazolium bromide | 2.92 | |
| 3-(2-methoxy-2-oxoethyl)-4-methyl-5-(2-hydroxyethyl)thiazolium bromide | | 38% |
| 3-(2-phenyl-2-oxoethyl)-4-methyl-5-(2-hydroxyethyl)thiazolium bromide | | 36% |
| 3-[2-(4'-bromophenyl)-2-oxoethyl]-4-methyl-5-(2-hydroxyethyl)thiazolium bromide | 4.51 | |
| 3-(2-methoxy-2-oxoethyl)benzothiazolium bromide | | 35% |
| 3-(carboxymethyl)benzothiazolium bromide | | 16% |
| 2,3-(diamino)benzothiazolium mesitylenesulfonate | 0.0749 | |
| 3-(2-amino-2-oxoethyl)thiazolium bromide | 0.226 | |
| 3-(2-amino-2-oxoethyl)-4-methylthiazolium bromide | 0.116 | |
| 3-(2-amino-2-oxoethyl)-5-methylthiazolium bromide | 0.0289 | |
| 3-(2-amino-2-oxoethyl)4,5-dimethylthiazolium bromide | 0.338 | |
| 3-(2-amino-2-oxoethyl)benzothiazolium bromide | 0.618 | |
| 3-(2-amino-2-oxoethyl)4-methyl-5-(2-hydroxyethyl)thiazolium bromide | 1.256 | |
| 3-amino-5-(2-hydroxyethyl)-4-methylthiazolium mesitylenesulfonate | 0.026 | |
| 3-(2-phenyl-2-oxoethyl)thiazolium bromide | | 34% |

The above experiments suggest that this type of drug therapy may have benefit in reducing the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints. This therapy might retard atherosclerosis and connective tissue changes that occur with diabetes and aging. Both topical, oral, and parenteral routes of administration to provide therapy locally and systemically are contemplated.

EXAMPLE 5

In order to ascertain the ability of the compounds of the instant invention to "break" or reverse already formed advanced glycosylation endproducts, a novel sandwich enzyme immunoassay was developed which detects breaking of AGE (Advanced glycosylation endproduct) moieties from AGE-crosslinked protein. The assay utilizes collagen-coated 96 will microtiter plates that are obtained commercially. AGE-modified protein (AGE-BSA) is incubated on the collagen-coated wells for four hours, is washed off the wells with PBS-Tween and the test compounds are added. Following an incubation period of 16 hours (37° C.) AGE-breaking is detected using an antibody raised against AGE-ribonuclease or with an antibody against BSA. Positive results in this assay indicate compounds that are capable of reducing the amount of AGE-BSA previously crosslinked to the collagen. Details of the assay are as follows:

MATERIALS

Immunochemicals and Chemicals

Bovine Serum Albumin (Type V), (BSA) Calbiochem Dextrose Superbloc, Pierce, Inc. Rabbit anti(AGE-RNAse) Rabbit anti-Bovine Serum Albumin Horseradish Peroxidase (HRP)-Goat-anti-rabbit), Zymed HRP substrate buffer, Zymed ABTS chromogen, Zymed Phosphate Buffer Saline Tween 20, Sigma

Equipment

ELISA Plate Washer, Dynatech ELISA Plate Reader, Dynatech Precision Water Bath Corning digital pH meter

Glassware and Plasticware

Finneppette Multichannel Pipettor, Baxter Eppendorf pipettes, Baxter Eppendorf repeater pipette, Baxter Pipetter tips for Finneppetter, Baxter Pipetter tips for Eppendorf, Baxter Glass test tubes, 13×100 mm; Baxter Mylar Sealing Tape for 96 well plates, Corning Biocoat Cellware Rat Tail Collagen Type-1 coated 96-well plates, Collaborative Biomedical Products

METHODS

Preparation of Solutions and Buffers

1. AGE-BSA stock solutions were prepared as follows. Sodium phosphate buffer (0.4M) was prepared by dissolving 6 grams of monobasic sodium phosphate in 100 ml of distilled water, 7 grams of dibasic sodium phosphate (0.4M) in 100 ml of distilled water and adjusting the pH of the dibasic solution to 7.4 with the monobasic solution. Sodium azide (0.02 grams) was added per 100 ml volume to inhibit bacterial growth. The BSA solution was prepared as follows: 400 mg of Type V BSA (bovine serum albumin) was added for each ml of sodium phosphate buffer (above). A 400 mM glucose solution was prepared by dissolving 72 grams of dextrose in 100 ml of sodium phosphate buffer (above). The BSA and glucose solutions were mixed 1:1 and incubated at 37° C. for 12 weeks. The pH of the incubation mixture was monitored weekly and adjusted to pH 7.4 if necessary. After 12 weeks, the AGE-BSA solution was dialyzed against PBS for 48 hours with four buffer changes, each at a 1:500 ratio of solution to dialysis buffer. Protein concentration was determined by the micro-Lowry method. The AGE-BSA stock solution was aliquoted and stored at −20° C. Dilute solutions of AGE-BSA were unstable when stored at −20° C.

2. Working solutions for crosslinking and breaking studies were prepared as follows. Test compounds were dissolved in PBS and the pH was adjusted to pH 7.4 if necessary. AGE-BSA stock solution was diluted in PBS to measure maximum crosslinking and in the inhibitor solution for testing inhibitory activity of compounds. The concentration of AGE-BSA necessary to achieve the optimum sensitivity was determined by initial titration of each lot of AGE-BSA.

3. Wash buffer ("PBS-Tween") was prepared as follows. PBS was prepared by dissolving the following salts in one liter of distilled water: NaCl, 8 grams; KCl, 0.2 gram, $KH_2PO_4$. 1.15 grams; $NaN_3$, 0.2 gram. Tween-20 was added to a final concentration of 0.05% (vol/vol).

4. Substrates for detection of secondary antibody binding were prepared by diluting the HRP substrate buffer 1:10 in distilled water and mixing with ABTS chromogen 1:50 just prior to use.

Assay Procedures

1. Biocoat plates were blocked With 300 μl of "Superbloc". Plates were blocked for one hour at room temperature and were washed with PBS-Tween three times with the Dynatech platewasher before addition of test reagents.

2. Each experiment was set up in the following manner. The first three wells of the Biocoat plate were used for the reagent blank. Fifty microliters of solutions containing either AGE-BSA alone or in combination with the test compounds: and corresponding blanks with BSA were added to wells in triplicate. The plate was incubated at 37° C. for four hours and washed with PBS-Tween three times. Fifty microliters of PBS was added to the control wells and 50 μl of the test "AGE Breaker" compounds was added to the test wells. The plate was incubated overnight (approximately 16 hours) with the test "AGE breaker" compound, followed bywashing in PBS before addition of primary antibody (below).

3. Each lot of primary antibody (anti-AGE RNase or anti-BSA) was tested for optimum binding capacity in this assay by preparing serial dilutions (1:500 to 1:2000) and plating 50 μl of each dilution in the wells of Biocoat plates. Optimum primary antibody was determined from saturation kinetics. Fifty microliters of primary antibody of appropriate dilution, determined by initial titration, was added and incubated for one hour at room temperature. The plate was then washed with PBS-Tween.

4. Plates were incubated with the secondary antibody, HRP-(Goat anti-rabbit), which was diluted 1:4000 in PBS and used as the final secondary antibody. The incubation was performed at room temperature for thirty minutes.

5. Detection of maximum crosslinking and breaking of AGE crosslinking was performed as follows. HRP substrate (100 ul) was added to each well of the plate and was incubated at 37° C. for fifteen minutes. Readings were taken in the Dynatech ELISA-plate reader. The sample filter was set to "1" and the reference filter was set to "5".

STANDARD OPERATING PROCEDURE

Preliminary Steps

1. Titrate each new lot of AGE-BSA preparation as described in Table 4 and determine the optimum AGE-BSA concentration for the ELISA assay from saturation kinetics.

2 At the beginning of the day, flush the plate washer head with hot water, rinse with distilled water and 50% ethanol. Fill the buffer reservoir of the plate washer with PBS-Tween (0.05%) and purge the system three times before use.

3. Prepare an assay template for setting up the experiment as described under "Assay Setup", #2, below.

Assay Setup

1. Warm Superbloc reagent to 37° C. Add 300 μl of Superbloc to each well of the Biocoat plate and let stand for sixty minutes at 37° C. Wash the wells three times with PBS-Tween (0.05%). Turn the plate 180 degrees and repeat this wash cycle.

2. Dilute the AGE-BSA in PBS so that 50 μl of the diluted sample will contain the amount of AGE-BSA necessary for minimum crosslinking and inhibition by pimagedine (aminoguanidine), as determined by initial titration described above. Prepare negative controls by dissolving non-browned BSA in PBS at the same concentration as the AGE-BSA. Add 50 μl of AGE-BSA or BSA to each well which correspond to the "AGE-BSA" and "BSA" labels on the template.

3. Dissolve the test compounds in PBS at 30 mM concentration for preliminary evaluation. The pH must be checked and adjusted to 7.4 when necessary. Pretreat the collagen-coated plates with AGE-BSA to obtain maximum crosslinking. Prepare negative controls for inhibition experiments by dissolving BSA in the inhibition solution at the same protein concentration as that used for AGE-BSA. Add 50 μl of AGE-BSA or BSA in the inhibitor solutions to the wells which correspond to "ALT#+AGE-BSA" and to "ALT# blank", respectively, on the template. Incubate the plate at 37° C. for four hours. Following covalent binding of AGE-BSA to the plates, wash the plates with PBS-Tween in preparation of the detection reaction (below).

4. Binding of primary antibody to the Biocoat plates is carried out as follows. At the end of the four hour incubation, the wells are washed with PBS-Tween. Appropriate dilutions (as determined by initial titration) of the rabbit-anti-AGE-RNase or rabbit-anti-BSA antibodies were prepared in PBS, and 50 μl is added to each well and the plate is allowed to stand at room temperature for sixty minutes.

6. Color development was carried out as follows. Plates are washed as in Step 4 above. Dilute the HRP-substrate buffer 1:10 in water. Add 200 μl of ABTS solution, mix well and add 100 μl of this reagent to each well. Incubate the plate at 37° C. for fifteen minutes. Read the optical density at 410 nm with the sample filter set to "1" and the reference filter set to "5" on the Dynatech ELISA plate reader. Calculate the percent inhibition by the compound as described above. Compounds which are found to reduce the amount of immunoreactivity are considered to be therapeutically useful insofar as they reverse and reduce the levels of advanced glycosylation endproducts.

| Test Compound | $IC_{50}$ (mM) Anti-AGE/ Anti-BSA | % Inhibition Anti-AGE/Anti-BSA (at mM) |
|---|---|---|
| 3-aminothiazolium mesitylenesulfonate | 0.05/3.0 | |
| 3-amino-4,5-dimethylamino-thiazolium mesitylenesulfonate | | 46%/ND (10) |
| 2,3-diaminothiazolinium mesitylenesulfonate | 0.0006/0.18 | |
| 3-(2-methoxy-2-oxoethyl)-thiazolium bromide | | 38%/41% (30) |
| 3-(2-methoxy-2-oxoethyl)-4,5-dimethylthiazolium bromide | | 50%/30% (30) |
| 3-(2-methoxy-2-oxoethyl)-4-methylthiazolium bromide | | 54%/41% (30) |
| 3-(2-phenyl-2-oxoethyl)-4-methylthizolium bromide | 0.23/0.30 | |
| 3-(2-phenyl-2-oxoethyl)-4,5-dimethylthiazolium bromide | | 56%/ND (30) |
| 3-amino-4-methylthiazolium mesitylenesulfonate | | 55%/ND (30) |
| 3-(2-methoxy-2-oxoethyl)-5-methyl)thiazolium bromide | | 72%/27% (30) |
| 3-[2-(4'-bromophenyl)-2-oxoethyl]thiazolium bromide | | 76%/25% (30) |
| 3-(2-phenyl-2-oxoethyl)-4-methyl-5-(2-hydroxyethyl)thiazolium bromide | 14.3/112.0 | |
| 3-benzyl-5-(2-hydroxyethyl)-4-methylthiazolium chloride | 0.42/0.55 | |
| 3-(2-methoxy-2-oxoethyl)-benzothiazolium bromide | 1.20/25.9 | |
| 3-(carboxymethyl)benzothiazolium bromide | | 63.7%/17.9% (30) |
| 2,3-(diamino)benzothiazolium mesitylenesulfonate | | 75%/35% (30) |

-continued

| Test Compound | $IC_{50}$ (mM) Anti-AGE/ Anti-BSA | % Inhibition Anti-AGE/Anti-BSA (at mM) |
|---|---|---|
| 3-(2-amino-2-oxoethyl)-4-methylthiazolium bromide | 4.70/38.6 | |
| 3-(2-amino-2-oxoethyl)-4,5-dimethylthiazolium bromide | | 69%/75% (30) |
| 3-(2-amino-2-oxoethyl)benzothiazolium bromide | 0.14/0.52 | |
| 3-(2-amino-2-oxoethyl)-4-methyl-5-(2-hydroxyethyl)-thiazolium bromide | 0.012/0.120 | |
| 3-amino-5-(2-hydroxyethyl)-4-methylthiazolium mesitylenesulfonate | 0.18/0.50 | |
| 3-(2-methyl-2-oxoethyl)-thiazolium chloride | 0.000036/0.260 | |
| 3-(2-phenyl-2-oxoethyl)-thiazolium bromide | 0.020/0.014 | |

EXAMPLE 6

| | mg/tablet |
|---|---|
| Compound of Formula I | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a 11/32" punch with a hardness of 4 kg. These tablets will disintegrate within a half hour according to the method described in USP XVI.

EXAMPLE 7

| Lotion | mg/g |
|---|---|
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 8

| Oral Rinse | |
|---|---|
| Compound of Formula I: | 1.4% |
| Chlorhexidine gluconate | 0.12% |
| Ethanol | 11.6% |
| Sodium saccharin | 0.15% |
| FD&C Blue No. 1 | 0.001% |
| Peppermint oil | 0.5% |

-continued

| Oral Rinse | |
|---|---|
| Glycerine | 10.0% |
| Tween 60 | 0.3% |
| Water to | 100% |

EXAMPLE 9

| Toothpaste | |
|---|---|
| Compound of Formula I: | 5.5% |
| Sorbitol, 70% in water | 25% |
| Sodium saccharin | 0.15% |
| Sodium lauryl sulfate | 1.75% |
| Carbopol 934, 6% dispersion in | 15% |
| Oil of Spearmint | 1.0% |
| Sodium hydroxide, 50% in water | 0.76% |
| Dibasic calcium phosphate dehydrate | 45% |
| Water to | 100% |

EXAMPLE 10

To further study the ability of inhibitors of nonenzymatic browning to prevent the discoloration of protein on a surface, such as that which occurs on the tooth surface, the following surface browning experiment is performed. As a substitute for a pellicle-covered tooth surface, unexposed and developed photographic paper is used to provide a fixed protein (gelatin, i.e., collagen) surface on a paper backing. Five millimeter circles are punched and immersed for one week at 50° C. in a solution of 100 mM glucose-6-phosphate in a 0.5M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or a compound of Formula I are included. After incubation, the gelatin/paper disks are rinsed with water, observed for brown color, and photographed.

Incubation of the disks in glucose-6-phosphate alone shows slight brown color versus disks soaked in buffer alone. Inclusion of chlorhexidine (in the form of Peridex®at a final concentration of 0.04% chlorhexidine) shows significant browning. Addition of a compound of Formula I to the chlorhexidine completely inhibits browning of the gelatin, as does inclusion of a compound of Formula I in the absence of chlorhexidine.

The slight brown color formed by the action of glucose-6-phosphate on the gelatin surface alone and its prevention by a compound of Formula I demonstrates the utility of the present invention in preventing nonenzymatic browning of tooth surfaces. The enhanced browning in the presence of chlorhexidine and its prevention with a compound of Formula I demonstrates the utility of the present invention in preventing the anti-plaque agent-enhanced nonenzymatic browning which occurs with chlorhexidine.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A composition for inhibiting the advanced glycosylation of a target protein in the oral cavity comprising an effective amount of [a compound] *one or more compounds* selected from [the group consisting of] compounds of the formula*:*

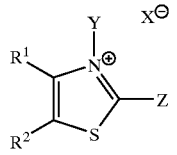

wherein $R^1$ and $R^2$ are independently [selected from the group consisting of] hydrogen, hydroxy(lower) alkyl, lower acyloxy(lower)alkyl, *or* lower alkyl, or $R_1$ and $R_2$ together with their ring carbons [may be] *form* an aromatic fused ring;

Z is hydrogen or an amino group;

Y is hydrogen, [or]

a group of the formula $$—CH_2C(=O)—R$$

wherein R is a lower alkyl, *lower* alkoxy, hydroxy, amino or aryl group*, and wherein, when R is aryl, at least one of $R^1$ and $R^2$ is other than hydrogen and $R^1$ and $R^2$ are not part of a un-substituted fused phenyl ring;* or a group of the formula $—CH_2R'$ wherein R' is hydrogen, or a lower alkyl, lower alkynyl or aryl group; *and*

X is a [halide, tosylate, methanesulfonate or mesitylenesulfonate ion; and mixtures thereof, and a carrier therefor] *pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups;* and a *pharmaceutically acceptable* carrier therefor.

2. The composition of claim 1 wherein [said compound has the formula wherein Y is a 2-phenyl-2-oxoethyl group] *R is aryl.*

3. The composition of claim [2] *1* wherein [said compound is 3-(2-phenyl-2-oxoethyl)thiazolium bromide or another biologically acceptable salt thereof] *X is a halide, tosylate, methanesulfonate or mesitylenesulfonate ion.*

4. The composition of claim 2 wherein said compound is *a* 3-(2-phenyl-2-oxoethyl)-4-methylthiazolium [bromide or another biologically acceptable] salt [thereof].

5. The composition of claim 2 wherein said compound is *a* 3-(2-phenyl-2-oxoethyl)-4,5-dimethylthiazolium [bromide or another biologically acceptable] salt [thereof].

6. The composition of claim 2 wherein said compound is *a* 3-(2-phenyl-2-oxoethyl)-5-methylthiazolium [bromide or another biologically acceptable] salt [thereof].

7. The composition of claim [2] *1* wherein [said compound is 3-(2-phenyl-2-oxoethyl)-benzothiazolium bromide or another biologically acceptable salt thereof] *X is a halide ion.*

8. The composition of claim 1 wherein Y is a 2-amino-2-oxoethyl group.

9. The composition of claim 8 wherein said compound is *a* 3-(2-amino-2-oxoethyl)-4-methylthiazolium [bromide or another biologically acceptable] salt [thereof].

10. The composition of claim 8 wherein said compound is *a* 3-(2,-amino-2-oxoethyl)benzothiazolium [bromide or another biologically acceptable salt thereof].

11. The composition of claim 8 wherein said compound is *a* 3-(2-amino-2-oxoethyl)-4-methyl-5-(2-hydroxyethyl) thiazolium [bromide or another biologically acceptable] salt [thereof].

12. The composition of claim 1 wherein said compound is *a* 3-(2-methyl-2-oxoethyl)thiazolium [chloride or another biologically acceptable] salt [thereof].

13. A pharmaceutical composition for administration to an animal [to inhibit the advanced glycosylation of a target protein within said animal], comprising a pharmaceutically effective amount of [a compound] *one or more compounds* selected from [the group consisting of] compounds of the formula:

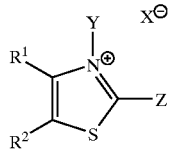

wherein $R^1$ and $R^2$ are independently [selected from the group consisting of] hydrogen, hydroxy(lower)alkyl, (lower) acyloxy(lower)alkyl, *or* lower alkyl, or $R^1$ and $R^2$ together with their ring carbons [may be] *form* an aromatic fused ring;

Z is hydrogen or an amino group;

Y is hydrogen, [or]

a group of the formula —$CH_2C(=O)R$ wherein R is a lower alkyl, *lower* alkoxy, hydroxy, amino or an aryl group *and wherein, when R is aryl, at least one of $R^1$ and $R^2$ is other than hydrogen and $R^1$ and $R^2$ are not part of a un-substituted fused phenyl ring;* or a group of the formula —$CH_2R'$ wherein R' is hydrogen, or a lower alkyl, lower alkynyl, or aryl group; *and*

X is a [halide, tosylate, methanesulfonate or mesitylenesulfonate ion; and mixtures thereof,] *pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups:* and a pharmaceutically acceptable carrier therefor.

14. The composition of claim 13 wherein [said compound has the formula wherein Y is a 2-phenyl-2-oxoethyl group] *R is aryl.*

15. The composition of claim [14] *13* wherein [said compound is 3-(2-phenyl-2-oxoethyl)thiazolium bromide or another biologically acceptable salt thereof] *X is a halide, tosylate, methanesulfonate or mesitylenesulfonate ion.*

16. The composition of claim 14 wherein said compound is *a* 3-(2-phenyl-2-oxoethyl)4-methylthiazolium [bromide or another biologically acceptable] salt [thereof].

17. The composition of claim 14 wherein said compound is *a* 3-(2-phenyl-2-oxoethyl)-4,5-dimethylthiazolium [bromide or another biologically acceptable] salt [thereof].

18. The composition of claim 14 wherein said compound is *a* 3-(2-phenyl-2-oxoethyl)-5-methylthiazolium [bromide or another biologically acceptable] salt [thereof].

19. The composition of claim [14] *13* wherein [said compound is 3-(2-phenyl-2-oxoethyl)-benzothiazolium bromide or another biologically acceptable salt thereof] *X is a halide ion.*

20. The composition of claim 14 wherein Y is a 2-amino-2-oxoethyl group.

21. The composition of claim 20 wherein said compound is *a* 3-(2-amino-2-oxoethyl)-4-methylthiazolium [bromide or another biologically acceptable] salt [thereof].

22. The composition of claim 20 wherein said compound is *a* 3-(2-amino-2-oxoethyl)benzothiazolium [bromide or another biologically acceptable] salt [thereof].

23. The composition of claim 20 wherein said compound is *a* 3-(2-amino-2-oxoethyl)-4-methyl-5-(2-hydroxyethyl) thiazolium [bromide or another biologically acceptable] salt [thereof].

24. The composition of claim 13 wherein said compound is *a* 3-(2-methyl-2-oxoethyl)thiazolium [chloride or another biologically acceptable] salt [thereof].

25. A method for inhibiting the advanced glycosylation of a target protein comprising contacting the target protein with an effective amount of composition comprising [a compound] *one or more compounds* selected from [the group consisting of] compounds of the formula:

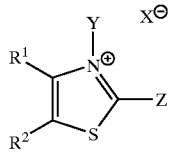

wherein $R^1$ and $R^2$ are independently [selected from the group consisting of] hydrogen, hydroxy(lower) alkyl, lower acyloxy(lower)alkyl, *or* lower alkyl, or $R^1$ and $R^2$ together with their ring carbons [may be] *form* an aromatic fused ring;

Z is hydrogen or an amino group;

Y is hydrogen, [or]

a group of the formula

—$CH_2C(=O)$—R wherein R is a lower alkyl, *lower* alkoxy, hydroxy, amino or aryl group; or a group of the formula —$CH_2$—R' wherein R' is hydrogen, or a lower alkyl, lower alkynyl or aryl group; *and*

X is a [halide, rosylate, methanesulfonate or mesitylenesulfonate ion; and mixtures thereof, and a carrier therefor] *pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups.*

26. The method of claim 25 wherein [said compound has the formula wherein Y is a 2-phenyl-2-oxoethyl group] *R is aryl.*

27. The method of claim 26 wherein said compound is *a* 3-(2-phenyl-2-oxoethyl)thiazolium [bromide or another biologically acceptable] salt [thereof].

28. The method of claim 26 wherein said compound is *a* 3-(2-phenyl-2-oxoethyl)-4-methylthiazolium [bromide or another biologically acceptable] salt [thereof].

29. The method of claim 26 wherein said compound is *a* 3-(2-phenyl-2-oxoethyl)-4,5-dimethylthiazolium [bromide or another biologically acceptable] salt [thereof].

30. The method of claim 26 wherein said compound is *a* 3-(2-phenyl-2-oxoethyl)-5-methylthiazolium [bromide or another biologically acceptable] salt [thereof].

31. The method of claim 26 wherein said compound is *a* 3-(2-phenyl-2-oxoethyl)-benzothiazolium [bromide, or another biologically acceptable] salt [thereof].

32. The method of claim 25 wherein Y is a 2-amino-2-oxoethyl group.

33. The method of claim 32 wherein said compound is *a* 3-(2-amino-2-oxoethyl)-4-methylthiazolium [bromide or another biologically acceptable] salt [thereof].

34. The method of claim 32 wherein said compound is *a* 3-(2-amino-2-oxoethyl)benzothiazolium [bromide or another biologically acceptable] salt [thereof].

35. The method of claim 32 wherein said compound is *a* 3-(2-amino-2-oxoethyl)-4-methyl-5-(2-hydroxyethyl) thiazolium [bromide or another biologically acceptable] salt [thereof].

36. The method of claim 25 wherein said compound is *a* 3-(2-methyl-2-oxoethyl)thiazolium [chloride or another biologically acceptable] salt [thereof].

37. A method for treating *diabetes or treating or ameliorating adverse sequelae of diabetes in* an animal [to inhibit the formation of advanced glycosylation endproducts of a target protein within said animal], said method comprising administering [an] *a diabetes treating or adverse sequelae of diabetes treating or ameliorating* effective amount of a pharmaceutical composition, said pharmaceutical composition comprising [a compound] *one or more compounds* selected from [the group consisting of] compounds of the formula:

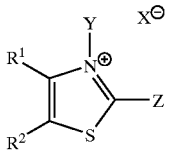

wherein $R^1$ and $R^2$ are independently [selected from the group consisting of] hydrogen, hydroxy (lower)alkyl, lower acyloxy(lower)alkyl, *or* lower alkyl or $R^1$ and $R^2$ together with their ring carbons [may be] *form* an aromatic fused ring;

Z is hydrogen or an amino group;

Y is hydrogen, [or]

a group of the formula $—CH_2C(=O)—R$ wherein R is a lower alkyl, *lower* alkoxy, hydroxy, amino or aryl group; or a group of the formula $CH_2$—R' wherein R' is hydrogen, or a lower alkyl, lower alkynyl or aryl group; *and*

X is a [halide, tosylate, methanesulfonate or mesitylenesulfonate ion; and mixtures thereof, and a pharmaceutically acceptable carrier therefor] *pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups.*

38. The method of claim 37 wherein [said compound has the formula wherein Y is a 2-phenyl-2-oxoethyl group] *R is aryl.*

39. The method of claim 38 wherein said compound [is 3-(2-phenyl-2-oxoethyl)thiazolium bromide or another biologically acceptable] *has the formula wherein Y is a 2-phenyl-2-oxoethyl group* salt [thereof].

40. The method of claim 38 wherein said compound is *a* 3-(2-phenyl-2-oxoethyl)-4-methylthiazolium [bromide or another biologically acceptable] salt [thereof].

41. The method of claim 38 wherein said compound is *a* 3-(2-phenyl-2-oxoethyl)-4,5-dimethylthiazolium [bromide or another biologically acceptable] salt [thereof].

42. The method of claim 38 wherein said compound is *a* 3-(2-phenyl-2-oxoethyl)-5-methylthiazolium [bromide or another biologically acceptable] salt [thereof].

43. The method of claim 38 wherein said compound is *a* 3-(2-phenyl-2-oxoethyl)-benzothiazolium [bromide or another biologically acceptable] salt [thereof].

44. The method of claim 37 wherein Y is a 2-amino-2-oxoethyl group.

45. The method of claim 44 wherein said compound is *a* 3-(2-amino-2-oxoethyl)-4-methylthiazolium [bromide or another biologically acceptable] salt [thereof].

46. The method of claim 44 wherein said compound is *a* 3-(2-amino-2-oxoethyl)benzothiazolium [bromide or another biologically acceptable] salt [thereof].

47. The method of claim 45 wherein said compound is *a* 3-(2-amino-2-oxoethyl)-4-methyl-5-(2-hydroxyethyl) thiazolium [bromide or another biologically acceptable] salt [thereof].

48. The method of claim 37 wherein said compound is *a* 3-(2-methyl-2-oxoethyl)thiazolium [chloride or another biologically acceptable salt thereof.].

49. A method of inhibiting the discoloration of teeth [resulting from non-enzymatic browning in the oral cavity] which comprises administration of [an amount] *a teeth discloration inhibiting* effective [to inhibit the formation of advanced glycosylation endproducts] *amount* of a composition comprising [a compound] *one or more compounds* selected from [the group consisting of] compounds of the formula:

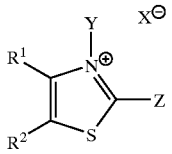

wherein $R^1$ and $R^2$ are independently [selected from the group consisting of] hydrogen, hydroxy(lower)alkyl, lower acyloxy(lower)alkyl, lower acyloxy(lower)alkyl, lower acyloxy(lower)alkyl, *or* lower alkyl, or $R^1$ and $R^2$ together with their ring carbons [may be] *form* an aromatic fused ring;

Z is hydrogen or an amino group;

Y is hydrogen, [or]

a group of the formula $—CH_2C(=O)—R$ wherein R is a lower alkyl, *lower* alkoxy, hydroxy, amino or aryl group; or a group of the formula $CH_2$—R' wherein R' is hydrogen, or a lower alkyl, lower alkynyl or aryl group; *and*

X is [a halide, tosylate, methanesulfonate or mesitylenesulfonate ion; and mixtures thereof, and a pharmaceutically acceptable carrier therefor] *an anion, wherein said fused aromatic rings or aryl groups can be substituted with up to two groups selected from halo, hydroxy, loweralkoxy or di(loweralkyl)amino groups.*

50. A compound of the formula:

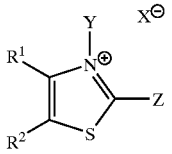

wherein Y and Z are both amino groups and $R^1$ and $R^2$ are independently selected from the group consisting of hydrogen, hydroxy(lower)alkyl, lower alkyl, or $R^1$ and $R^2$ together with their ring carbons may be an aromatic fused ring;

and X is [a halide, tosylate, methanesulfonate or mesitylenesulfonate ion] *an anion.*

51. The compound according to claim 50 which is *a* 2,3-diaminothiazolium [mesitylenesulfonate].

52. The compound according to claim 50 which is *a* 2,3-diaminobenzothiazolium [mesitylenesulfonate].

53. A compound of the formula:

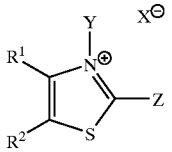

wherein $R^1$ and $R^2$ are independently [selected from the group consisting of] hydrogen, hydroxy(lower)alyl, lower acyloxy(lower)alkyl, *or* lower alkyl, or $R^1$ and $R^2$ together with their ring carbons may be an aromatic fused ring;

Z is hydrogen or an amino group;

Y is an alkynylmethyl group; and

X is [a halide, tosylate, methanesulfonate or mesitylenesulfonate ion] *an anion.*

54. A compound of the formula:

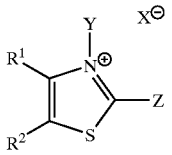

wherein $R^1$ and $R^2$ are independently [selected from the group consisting of] hydrogen, hydroxy(lower)alkyl, lower acyloxy(lower)alkyl, *or* lower alkyl, or $R^1$ and $R^2$ together with their ring carbons [may be] *form* an aromatic fused ring;

Z is hydrogen or an amino group;

Y is a 2-amino-2-oxoethyl group; and

X is [a halide, tosylate, methanesulfonate or mesitylenesulfonate ion] *an anion.*

55. The compound according to claim 54 which is *a* 3-(2-amino-2-oxoethyl)-4-methylthiazolium [bromide or another biologically acceptable] salt [thereof].

56. The compound according to claim 54 which is *a* 3-(2-amino-2-oxoethyl)benzothiazolium [bromide or another biologically acceptable] salt [thereof].

57. The compound according to claim 54 which is *a* 3-(2-amino-2-oxoethyl)-4-methyl-5-(2-hydroxyethyl) thiazolium [bromide or another biologically acceptable] salt [thereof].

*58. A method of treating or ameliorating kidney damage in an animal, said method comprising administering an kidney treating or ameliorating effective amount of a pharmaceutical composition, said pharmaceutical composition comprising one or more compounds selected from compounds of the formula:*

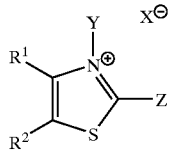

*wherein*

*$R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring:*

*Z is hydrogen or an amino group;*

*Y is*

*hydrogen,*

*a group of the formula*

$$-CH_2C(=O)-R$$

*wherein R is a lower alkyl, lower lower alkoxy, hydroxy, amino or aryl group; or*

*a group of the formula $CH_2$—R′*

*wherein R′ is hydrogen, or a lower alkyl, lower alkynyl or aryl group; and*

*X is a pharmaceutically acceptable anion,*

*wherein the fused aromatic rings or aryl groups of $R^1$, $R^2$, R or R′ may be substituted with up to two groups selected from halo, hydroxy, loweralkoxy or di(loweralkyl)amino groups.*

*59. The method of claim 58 wherein X is a halide, tosylate, methanesulfonate or mesitylenesulfonate ion.*

*60. The method of claim 58 wherein Z is hydrogen.*

*61. The method of claim 58 wherein R is aryl.*

*62. The method of claim 61 wherein Z is hydrogen.*

*63. The method of claim 61 wherein said compound is a 3-(2-phenyl-2-oxoethyl)-4-methylthiazolium.*

*64. The method of claim 61 wherein said compound is a 3-(2-phenyl-2-oxoethyl)-4,5-dimethylthiazolium.*

*65. The method of claim 61 wherein said compound is a 3-(2-phenyl-2-oxoethyl)-5-methylthiazolium.*

*66. The method of claim 61 wherein said compound is a 3-(2-phenyl-2-oxoethyl)-benzothiazolium.*

*67. The method of claim 58 wherein Y is a 2-amino-2-oxoethyl group.*

*68. The method of claim 58, comprising treating or preventing kidney damage in a human.*

*69. A method of treating or ameliorating damage to blood vasculature in an animal, said method comprising administering an blood vasculature treating or ameliorating effective amount of a pharmaceutical composition, said pharmaceutical composition comprising one or more compounds selected from compounds of the formula:*

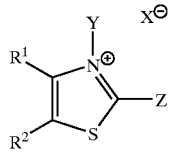

*wherein*

*$R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula $CH_2$—R'*

*wherein R' is hydrogen, or a lower alkyl, lower alkynyl or aryl group; and*

*X is a pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups.*

*70. The method of claim 69 wherein X is a halide, tosylate, methanesulfonate or mesitylenesulfonate ion.*

*71. The method of claim 69 wherein Z is hydrogen.*

*72. The method of claim 69 wherein R is aryl.*

*73. The method of claim 72 wherein Z is hydrogen.*

*74. The method of claim 72 wherein said compound is a 3-(2-phenyl-2-oxoethyl)-4-methylthiazolium.*

*75. The method of claim 72 wherein said compound is a 3-(2-phenyl-2-oxoethyl)-4,5-dimethylthiazolium.*

*76. The method of claim 72 wherein said compound is a 3-(2-phenyl-2-oxoethyl)-5-methylthiazolium.*

*77. The method of claim 72 wherein said compound is a 3-(2-phenyl-2-oxoethyl)-benzothiazolium.*

*78. The method of claim 69 wherein Y is a 2-amino-2-oxoethyl group.*

*79. The method of claim 69, comprising treating or preventing damage to blood vasculature in a human.*

*80. A method of improving the elasticity or reducing wrinkles of the skin of an animal, said method comprising topically administering an skin elasticity or wrinkle reducing effective amount of a pharmaceutical composition, said pharmaceutical composition comprising one or more compounds selected from compounds of the formula:*

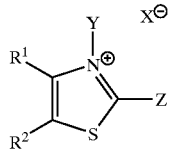

*wherein*

*$R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula $CH_2$—R'*

*wherein R' is hydrogen, or a lower alkyl, lower alkynyl or aryl group; and*

*X is a biologically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups.*

*81. The method of claim 80 wherein X is a halide, tosylate, methanesulfonate or mesitylenesulfonate ion.*

*82. The method of claim 80 wherein Z is hydrogen.*

*83. The method of claim 80 wherein R is aryl.*

*84. The method of claim 83 wherein Z is hydrogen.*

*85. The method of claim 83 wherein said compound is a 3-(2-phenyl-2-oxoethyl)-4-methylthiazolium.*

*86. The method of claim 83 wherein said compound is a 3-(2-phenyl-2-oxoethyl)-4,5-dimethylthiazolium.*

*87. The method of claim 83 wherein said compound is a 3-(2-phenyl-2-oxoethyl)-5-methylthiazolium.*

*88. The method of claim 83 wherein said compound is a 3-(2-phenyl-2-oxoethyl)-benzothiazolium.*

*89. The method of claim 80 wherein Y is a 2-amino-2-oxoethyl group.*

*90. The method of claim 80 comprising improving the elasticity or reducing wrinkles of the skin of a human.*

*91. A topical composition comprising one or more compounds selected from compounds of the formula:*

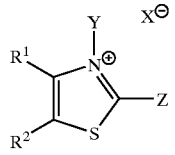

*wherein*

*$R^1$ and $R^2$ are independently hydrogen, hydroxy(lower) alkyl, lower acyloxy(lower)alkyl, or lower alkyl, or $R_1$ and $R_2$ together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula —$CH_2$R'*

*wherein R' is hydrogen, or a lower alkyl, lower alkynyl or aryl group; and*

*X is a biologically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups; and* a pharmaceutically acceptable carrier therefor suitable for topical administration.

92. The topical composition of claim 91 wherein X is a halide, tosylate, methanesulfonate or mesitylenesulfonate ion.

93. The topical composition of claim 91 wherein Z is hydrogen.

94. The topical composition of claim 91, wherein, when R is aryl, at least one of $R^1$ and $R^2$ is other than hydrogen and $R^1$ and $R^2$ are not part of a un-substituted fused phenyl ring.

95. The topical composition of claim 94 wherein Z is hydrogen.

96. The topical composition of claim 95 wherein R is aryl.

97. The topical composition of claim 96 wherein said compound is a 3-(2-phenyl-2-oxoethyl)thiazolium.

98. The topical composition of claim 96 wherein said compound is a 3-(2-phenyl-2-oxoethyl)-4-methylthiazolium.

99. The topical composition of claim 96 wherein said compound is a 3-(2-phenyl-2-oxoethyl)-4,5-dimethylthiazolium.

100. The topical composition of claim 96 wherein said compound is 3-(2-phenyl-2-oxoethyl)-4,5-dimethylthiazolium bromide.

101. The topical composition of claim 96 wherein said compound is a 3-(2-phenyl-2-oxoethyl)-5-methylthiazolium.

102. The topical composition of claim 96 wherein said compound is a 3-(2-phenyl-2-oxoethyl)-benzothiazolium.

103. The topical composition of claim 96 wherein Y is a 2-amino-2-oxoethyl group.

104. The topical composition of claim 103 wherein said compound is a 3-(2-amino-2-oxoethyl)-4-methylthiazolium.

105. The topical composition of claim 103 wherein said compound is a 3-(2,-amino-2-oxoethyl)benzothiazolium.

106. The topical composition of claim 103 wherein said compound is a 3-(2-amino-2-oxoethyl)-4-methyl-5-(2-hydroxyethyl)thiazolium.

107. A method of treating or ameliorating hypertension in an animal, said method comprising administering an hypertension treating or ameliorating effective amount of a pharmaceutical composition, said pharmaceutical composition comprising one or more compounds selected from compounds of the formula:

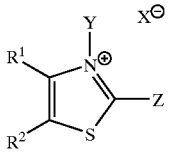

wherein $R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;

Z is hydrogen or an amino group;

Y is hydrogen, a group of the formula $$—CH_2C(=O)—R$$

wherein R is a lower alkyl, lower alkoxy, hydroxy, amino or aryl group; or a group of the formula $CH_2$—R′ wherein R′ is hydrogen, or a lower alkyl, lower alkynyl or aryl group; and

X is a pharmaceutically or biologically acceptable anion, wherein the fused aromatic rings or aryl groups of $R^1$, $R^2$, R or R′ may be substituted with up to two groups selected from halo, hydroxy, loweralkoxy or di(loweralkyl)amino groups.

108. The method of claim 107 wherein X is a halide, tosylate, methanesulfonate or mesitylenesulfonate ion.

109. The method of claim 107 wherein X is a halide ion.

110. The method of claim 107 wherein Z is hydrogen.

111. The method of claim 107 wherein R is aryl.

112. The method of claim 111 wherein Z is hydrogen.

113. The method of claim 111 wherein said compound is a 3-(2-phenyl-2-oxoethyl)-4-methylthiazolium.

114. The method of claim 111 wherein said compound is a 3-(2-phenyl-2-oxoethyl)-4,5-dimethylthiazolium.

115. The method of claim 111 wherein said compound is a 3-(2-phenyl-2-oxoethyl)-5-methylthiazolium.

116. The method of claim 111 wherein said compound is a 3-(2-phenyl-2-oxoethyl)-benzothiazolium.

117. The method of claim 107 wherein Y is a 2-amino-2-oxoethyl group.

118. The method of claim 107, comprising treating or ameliorating hypertension in a human.

119. A method of treating or ameliorating retinopathy in an animal, said method comprising administering an retinopathy treating or ameliorating effective amount of a pharmaceutical composition, said pharmaceutical composition comprising one or more compounds selected from compounds of the formula:

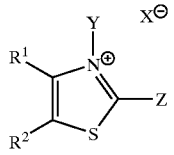

wherein $R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;

Z is hydrogen or an amino group;

Y is hydrogen, a group of the formula $$—CH_2C(=O)—R$$

wherein R is a lower alkyl, lower alkoxy, hydroxy, amino or aryl group; or a group of the formula $CH_2$—R′ wherein R′ is hydrogen, or a lower alkyl, lower alkynyl or aryl group; and

X is a pharmaceutically acceptable anion, wherein the fused aromatic rings or aryl groups of $R^1$, $R^2$, R or R′ may be substituted with up to two groups selected from halo, hydroxy, loweralkoxy or di(loweralkyl)amino groups.

120. The method of claim 119 wherein X is a halide, tosylate, methanesulfonate or mesitylenesulfonate ion.

121. The method of claim 119 wherein X is a halide ion.

122. The method of claim 119 wherein Z is hydrogen.

123. The method of claim 119 wherein R is aryl.

124. The method of claim 123 wherein Z is hydrogen.

125. The method of claim 123 wherein said compound is a 3-(2-phenyl-2-oxoethyl)-4-methylthiazolium.

126. The method of claim 123 wherein said compound is a 3-(2-phenyl-2-oxoethyl)-4,5-dimethylthiazolium.

127. The method of claim 123 wherein said compound is a 3-(2-phenyl-2-oxoethyl)-5-methylthiazolium.

128. The method of claim 123 wherein said compound is a 3-(2-phenyl-2-oxoethyl)-benzothiazolium.

129. The method of claim 120 wherein Y is a 2-amino-2-oxoethyl group.

130. The method of claim 120, comprising treating or ameliorating retinopathy in a human.

131. A method of treating damage to lens proteins in an animal, said method comprising administering an lens damage treating effective amount of a pharmaceutical composition, said pharmaceutical composition comprising one or more compounds selected from compounds of the formula:

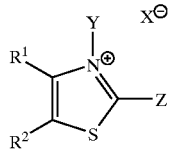

wherein $R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;

Z is hydrogen or an amino group;

Y is hydrogen, a group of the formula $$—CH_2\,C(=O)—R$$

wherein R is a lower alkyl, lower alkoxy, hydroxy, amino or aryl group; or a group of the formula $CH_2$—R′ wherein R′ is hydrogen, or a lower alkyl, lower alkynyl or aryl group; and

X is a pharmaceutically acceptable anion, wherein the fused aromatic rings or aryl groups of $R^1$, $R^2$, R or R′ may be substituted with up to two groups selected from halo, hydroxy, loweralkoxy or di(loweralkyl)amino groups.

132. The method of claim 131 wherein X is a halide, tosylate, methanesulfonate or mesitylenesulfonate ion.

133. The method of claim 131 wherein Z is hydrogen.

134. The method of claim 131 wherein R is aryl.

135. The method of claim 134 wherein Z is hydrogen.

136. The method of claim 134 wherein said compound is a 3-(2-phenyl-2-oxoethyl)-4-methylthiazolium.

137. The method of claim 134 wherein said compound is a 3-(2-phenyl-2-oxoethyl)-4,5-dimethylthiazolium.

138. The method of claim 134 wherein said compound is a 3-(2-phenyl-2-oxoethyl)-5-methylthiazolium.

139. The method of claim 134 wherein said compound is a 3-(2-phenyl-2-oxoethyl)-benzothiazolium.

140. The method of claim 131 wherein Y is a 2-amino-2-oxoethyl group.

141. The method of claim 131, comprising treating damage to lens proteins in a human.

142. A method of treating or ameliorating peripheral neuropathy in an animal, said method comprising administering an neuropathy treating or ameliorating effective amount of a pharmaceutical composition, said pharmaceutical composition comprising one or more compounds selected from compounds of the formula:

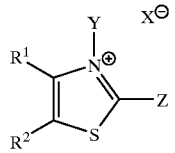

wherein $R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;

Z is hydrogen or an amino group;

Y is hydrogen, a group of the formula $$—CH_2C(=O)—R$$

wherein R is a lower alkyl, lower alkoxy, hydroxy, amino or aryl group; or a group of the formula $CH_2$—R′ wherein R′ is hydrogen, or a lower alkyl, lower alkynyl or aryl group; and

X is a pharmaceutically acceptable anion, wherein the fused aromatic rings or aryl groups of $R^1$, $R^2$, R or R′ may be substituted with up to two groups selected from halo, hydroxy, loweralkoxy or di(loweralkyl)amino groups.

143. The method of claim 142 wherein X is a halide, tosylate, methanesulfonate or mesitylenesulfonate ion.

144. The method of claim 142 wherein Z is hydrogen.

145. The method of claim 142 wherein R is aryl.

146. The method of claim 145 wherein Z is hydrogen.

147. The method of claim 145 wherein said compound is a 3-(2-phenyl-2-oxoethyl)-4-methylthiazolium.

148. The method of claim 145 wherein said compound is a 3-(2-phenyl-2-oxoethyl)-4,5-dimethylthiazolium.

149. The method of claim 145 wherein said compound is a 3-(2-phenyl-2-oxoethyl)-5-methylthiazolium.

150. The method of claim 145 wherein said compound is a 3-(2-phenyl-2-oxoethyl)-benzothiazolium.

151. The method of claim 142 wherein Y is a 2-amino-2-oxoethyl group.

152. The method of claim 142, comprising treating or ameliorating peripheral neuropathy in a human.

153. A composition adapted for ocular administration comprising one or more compounds selected from compounds of the formula:

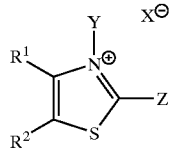

wherein $R^1$ and $R^2$ are independently hydrogen, hydroxy(lower) alkyl, lower acyloxy(lower)alkyl, or lower alkyl, or $R_1$ and $R_2$ together with their ring carbons form an aromatic fused ring;

Z is hydrogen or an amino group;

*Y is*

*hydrogen,*

*a group of the formula*

$$—CH_2C(=O)—R$$

*wherein R is a lower alkyl, lower alkoxy, hydroxy, amino or aryl group; or*

*a group of the formula* $—CH_2R'$

*wherein R′ is hydrogen, or a lower alkyl, lower alkynyl or aryl group; and*

*X is a pharmaceutically acceptable anion,*

*wherein the fused aromatic rings or aryl groups of* $R^1$, $R^2$, *R or R′ may be substituted with up to two groups selected from halo, hydroxy, loweralkoxy or di(loweralkyl)amino groups; and*

*a pharmaceutically acceptable carrier therefor suitable for topical administration.*

*154. The ocular composition of claim 153 wherein X is a halide, tosylate, methanesulfonate or mesitylenesulfonate ion.*

*155. The ocular composition of claim 153 wherein X is a halide ion.*

*156. The ocular composition of claim 153 wherein Z is hydrogen.*

*157. The ocular composition of claim 153, wherein, when R is aryl, at least one of* $R^1$ *and* $R^2$ *is other than hydrogen and* $R^1$ *and* $R^2$ *are not part of a un-substituted fused phenyl ring.*

*158. The ocular composition of claim 157 wherein Z is hydrogen.*

*159. The ocular composition of claim 158 wherein R is aryl.*

*160. The ocular composition of claim 158 wherein said compound is a 3-(2-phenyl-2-oxoethyl)thiazolium.*

*161. The ocular composition of claim 158 wherein said compound is a 3-(2-phenyl-2-oxoethyl)-4-methylthiazolium.*

*162. The ocular composition of claim 158 wherein said compound is a 3-(2-phenyl-2-oxoethyl)-4,5-dimethylthiazolium.*

*163. The ocular composition of claim 158 wherein said compound is 3-(2-phenyl-2-oxoethyl)-4,5-dimethylthiazolium bromide.*

*164. The ocular composition of claim 158 wherein said compound is a 3-(2-phenyl-2-oxoethyl)-5-methylthiazolium.*

*165. The ocular composition of claim 158 wherein said compound is a 3-(2-phenyl-2-oxoethyl)-benzothiazolium.*

*166. The ocular composition of claim 153 wherein Y is a 2-amino-2-oxoethyl group.*

*167. The ocular composition of claim 166 wherein said compound is a 3-(2-amino-2-oxoethyl)-4-methylthiazolium.*

*168. The ocular composition of claim 166 wherein said compound is a 3-(2,-amino-2-oxoethyl)benzothiazolium.*

*169. The ocular composition of claim 166 wherein said compound is a 3-(2-amino-2-oxoethyl)-4-methyl-5-(2-hydroxyethyl)thiazolium.*

*170. The composition of claim 1, wherein said compounds comprise up to 10% of the composition.*

*171. The composition of claim 13 wherein Z is hydrogen.*

*172. The composition of claim 14 wherein Z is hydrogen.*

*173. The composition of claim 13 wherein said compound is 3-(2-phenyl-2-oxoethyl)4-methylthiazolium bromide.*

*174. The composition of claim 13 wherein said compound is 3-(2-phenyl-2-oxoethyl)-4,5-dimethylthiazolium bromide.*

*175. The composition of claim 13 wherein said compound is 3-(2-phenyl-2-oxoethyl)-5-methylthiazolium bromide.*

*176. The composition of claim 13 wherein said compound is 3-(2-amino-2-oxoethyl)-4-methylthiazolium bromide.*

*177. The composition of claim 13 wherein said compound is 3-(2-amino-2-oxoethyl)benzothiazolium bromide.*

*178. The composition of claim 13 wherein said compound is 3-(2-amino-2-oxoethyl)-4-methyl-5-(2-hydroxyethyl) thiazolium bromide.*

*179. The composition of claim 13 wherein said compound is a 3-(2-methyl-2-oxoethyl)thiazolium chloride.*

*180. The method of claim 37, comprising treating diabetes or treating or ameliorating adverse sequelae of diabetes in a human.*

*181. The method of claim 37 wherein Z is hydrogen.*

*182. The method of claim 38 wherein Z is hydrogen.*

*183. A method of treating or ameliorating cataracts in an animal, said method comprising administering an lens damage treating or ameliorating effective amount of a pharmaceutical composition, said pharmaceutical composition comprising one or more compounds selected from compounds of the formula:*

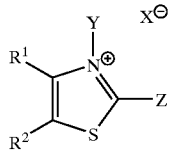

*wherein*

$R^1$ *and* $R^2$ *are independently hydrogen, hydroxy (lower) alkyl, lower acyloxy(lower)alkyl, or lower alkyl, or* $R^1$ *and* $R^2$ *together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula* $CH_2—R'$

*wherein R′ is hydrogen, or a lower alkyl, lower alkynyl or aryl group; and*

*X is a pharmaceutically acceptable anion,*

*wherein the fused aromatic rings or aryl groups of* $R^1$, $R^2$, *R or R′ may be substituted with up to two groups selected from halo, hydroxy, loweralkoxy or di(loweralkyl)amino groups.*

*184. The method of claim 183 wherein X is a halide, tosylate, methanesulfonate or mesitylenesulfonate ion.*

*185. The method of claim 183 wherein Z is hydrogen.*

*186. The method of claim 183 wherein R is aryl.*

*187. The method of claim 186 wherein Z is hydrogen.*

*188. The method of claim 186 wherein said compound is a 3-(2-phenyl-2-oxoethyl)-4-methylthiazolium.*

*189. The method of claim 186 wherein said compound is a 3-(2-phenyl-2-oxoethyl)-4,5-dimethylthiazolium.*

*190. The method of claim 186 wherein said compound is a 3-(2-phenyl-2-oxoethyl)-5-methylthiazolium.*

*191. The method of claim 186 wherein said compound is a 3-(2-phenyl-2-oxoethyl)-benzothiazolium.*

*192. The method of claim 183 wherein Y is a 2-amino-2-oxoethyl group.*

*193. The method of claim 183, comprising treating or ameliorating damage to lens proteins in a human.*

*194. A method of treating or ameliorating damage to a tissue caused by contact with elevated levels of reducing*

*sugars in an animal, said method comprising administering an treating or ameliorating effective amount of a pharmaceutical composition, said pharmaceutical composition comprising one or more compounds selected from compounds of the formula:*

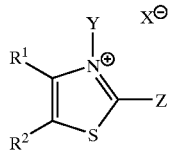

*wherein*

*$R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula $CH_2$—R'*

*wherein R' is hydrogen, or a lower alkyl, lower alkynyl or aryl group; and*

*X is a pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups.*

*195. The method of claim 194 wherein X is a halide, tosylate, methanesulfonate or mesitylenesulfonate ion.*

*196. The method of claim 194 wherein Z is hydrogen.*

*197. The method of claim 194 wherein R is aryl.*

*198. The method of claim 197 wherein Z is hydrogen.*

*199. The method of claim 197 wherein said compound is a 3-(2-phenyl-2-oxoethyl)-4-methylthiazolium.*

*200. The method of claim 197 wherein said compound is a 3-(2-phenyl-2-oxoethyl)-4,5-dimethylthiazolium.*

*201. The method of claim 197 wherein said compound is a 3-(2-phenyl-2-oxoethyl)-5-methylthiazolium.*

*202. The method of claim 197 wherein said compound is a 3-(2-phenyl-2-oxoethyl)-benzothiazolium.*

*203. The method of claim 194 wherein Y is a 2-amino-2-oxoethyl group.*

*204. The method of claim 194, comprising administering the compound intraperitoneally.*

*205. A method of treating or ameliorating stroke in an animal, said method comprising administering a stroke treating or ameliorating effective amount of a pharmaceutical composition, said pharmaceutical composition comprising one or more compounds selected from compounds of the formula:*

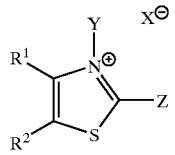

*wherein*

*$R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula $CH_2$—R'*

*wherein R' is hydrogen, or a lower alkyl, lower alkynyl or aryl group; and*

*X is a pharmaceutically acceptable anion,*

*wherein the fused aromatic rings or aryl groups of $R^1$, $R^2$, R or R' may be substituted with up to two groups selected from halo, hydroxy, loweralkoxy or di(loweralkyl)amino groups.*

*206. The method of claim 205 wherein X is a halide, tosylate, methanesulfonate or mesitylenesulfonate ion.*

*207. The method of claim 205 wherein Z is hydrogen.*

*208. The method of claim 205 wherein R is aryl.*

*209. The method of claim 208 wherein Z is hydrogen.*

*210. The method of claim 208 wherein said compound is a 3-(2-phenyl-2-oxoethyl)-4-methylthiazolium.*

*211. The method of claim 208 wherein said compound is a 3-(2-phenyl-2-oxoethyl)-4,5-dimethylthiazolium.*

*212. The method of claim 208 wherein said compound is a 3-(2-phenyl-2-oxoethyl)-5-methylthiazolium.*

*213. The method of claim 208 wherein said compound is a 3-(2-phenyl-2-oxoethyl)-benzothiazolium.*

*214. The method of claim 205 wherein Y is a 2-amino-2-oxoethyl group.*

*215. A method of treating or ameliorating osteoarthritis in an animal, said method comprising administering a osteoarthritis treating or ameliorating effective amount of a pharmaceutical composition, said pharmaceutical composition comprising one or more compounds selected from compounds of the formula:*

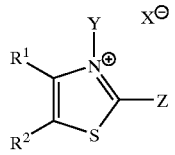

*wherein*

*$R^1$ and $R^2$ are independently hydrogen, hydroxy (lower) alkyl, lower acyloxy(lower)alkyl, or lower alkyl, or $R^1$ and $R^2$ together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula* $CH_2$—*R'*

*wherein R' is hydrogen, or a lower alkyl, lower alkynyl or aryl group; and*

*X is a pharmaceutically acceptable anion,*

*wherein the fused aromatic rings or aryl groups of* $R^1$, $R^2$, *R or R' may be substituted with up to two groups selected from halo, hydroxy, loweralkoxy or di(loweralkyl)amino groups.*

*216. The method of claim 205 wherein X is a halide, tosylate, methanesulfonate or mesitylenesulfonate ion.*

*217. The method of claim 205 wherein Z is hydrogen.*

*218. The method of claim 205 wherein R is aryl.*

*219. The method of claim 208 wherein Z is hydrogen.*

*220. The method of claim 208 wherein said compound is a 3-(2-phenyl-2-oxoethyl)-4-methylthiazolium.*

*221. The method of claim 208 wherein said compound is a 3-(2-phenyl-2-oxoethyl)-4,5-dimethylthiazolium.*

*222. The method of claim 208 wherein said compound is a 3-(2-phenyl-2-oxoethyl)-5-methylthiazolium.*

*223. The method of claim 208 wherein said compound is a 3-(2-phenyl-2-oxoethyl)-benzothiazolium.*

*224. The method of claim 205 wherein Y is a 2-amino-2-oxoethyl group.*

*225. A method of increasing red blood cell deformability in an animal, said method comprising administering a red blood cell deformability increasing effective amount of a pharmaceutical composition, said pharmaceutical composition comprising one or more compounds selected from compounds of the formula:*

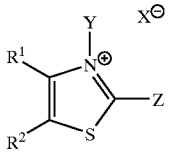

*wherein*

$R^1$ *and* $R^2$ *are independently hydrogen, hydroxy (lower) alkyl, lower acyloxy(lower)alkyl, or lower alkyl, or* $R^1$ *and* $R^2$ *together with their ring carbons form an aromatic fused ring;*

*Z is hydrogen or an amino group;*

*Y is*

*hydrogen,*

*a group of the formula*

$$—CH_2C(=O)—R$$

*wherein R is a lower alkyl, lower alkoxy, hydroxy, amino or aryl group; or*

*a group of the formula* $CH_2$—*R'*

*wherein R' is hydrogen, or a lower alkyl, lower alkynyl or aryl group; and*

*X is a pharmaceutically acceptable anion,*

*wherein the fused aromatic rings or aryl groups of* $R^1$, $R^2$, *R or R' may be substituted with up to two groups selected from halo, hydroxy, loweralkoxy or di(loweralkyl)amino groups.*

*226. The method of claim 205 wherein X is a halide, tosylate, methanesulfonate or mesitylenesulfonate ion.*

*227. The method of claim 205 wherein Z is hydrogen.*

*228. The method of claim 205 wherein R is aryl.*

*229. The method of claim 208 wherein Z is hydrogen.*

*230. The method of claim 208 wherein said compound is a 3-(2-phenyl-2-oxoethyl)-4-methylthiazolium.*

*231. The method of claim 208 wherein said compound is a 3-(2-phenyl-2-oxoethyl)-4,5-dimethylthiazolium.*

*232. The method of claim 208 wherein said compound is a 3-(2-phenyl-2-oxoethyl)-5-methylthiazolium.*

*233. The method of claim 208 wherein said compound is a 3-(2-phenyl-2-oxoethyl)-benzothiazolium.*

*234. The method of claim 205 wherein Y is a 2-amino-2-oxoethyl group.*

* * * * *